(12) United States Patent
Eggleston et al.

(10) Patent No.: US 6,583,283 B1
(45) Date of Patent: Jun. 24, 2003

(54) POLYMORPHIC FORMS OF CIPAMFYLLINE

(75) Inventors: Drake S Eggleston, Harlow (GB); Ian Robert Lynch, Harlow (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/529,865
(22) PCT Filed: Oct. 23, 1998
(86) PCT No.: PCT/US98/22451
§ 371 (c)(1),
(2), (4) Date: Aug. 15, 2000
(87) PCT Pub. No.: WO99/20625
PCT Pub. Date: Apr. 29, 1999

Related U.S. Application Data

(60) Provisional application No. 60/063,238, filed on Oct. 23, 1997.

(51) Int. Cl.[7] .................... C07D 473/16; A61K 31/522; A61P 37/08; A61P 11/06
(52) U.S. Cl. .................................................. 544/272
(58) Field of Search ........................ 514/263; 544/272

(56) References Cited

U.S. PATENT DOCUMENTS 5,734,051 A    3/1998    Spicer et al. ............... 544/118
5,981,535 A    11/1999   Spicer et al. ............... 544/118

FOREIGN PATENT DOCUMENTS

WO    WO 92/05175    4/1992
WO    WO 92/05176    4/1992

*Primary Examiner*—Mark L Berch
(74) *Attorney, Agent, or Firm*—Dara L. Dinner; Theodore R. Furman; Charles M. Kinzig

(57) ABSTRACT

This invention relates to novel crystalline polymorphic forms, Form I, II and IV of Cipamfylline, methods of preparation, and use thereof in the treatment of PDE4 and TNF mediated diseases. Cipamfylline is 1,3-di-cyclopropylmethyl-8-amino xanthine, and is represented by formula (I):

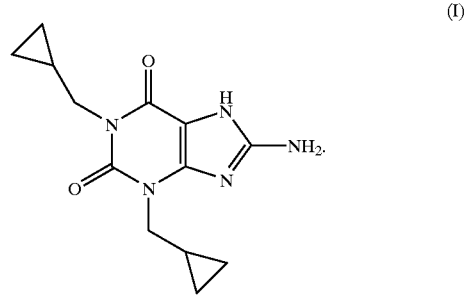

4 Claims, 43 Drawing Sheets

TABLE 4

Torsion Angle Tabulations for Forms II and IV

|  | Form II | Form IV |
|---|---|---|
| C7-N8-C10-C11 | 101.8(3) | 74.6(3) |
| C9-N8-C10-C11 | -84.6(3) | -99.5(3) |
| C5-N8-C10-C11 | 98.7(3) | 91.7(3) |
| C7-N6-C14-C15 | -80.2(3) | -85.1(3) |
| N8-C10-C11-C12 | -77.5(3) | 80.4(3) |
| N8-C10-C11-C13 | -146.6(3) | 149.8(3) |
| C10-C11-C12-C13 | -104.9(4) | -107.5(3) |
| N6-C14-C15-C16 | -88.5(3) | 89.4(3) |
| N6-C14-C15-C17 | -158.3(3) | 158.8(3) |
| C14-C15-C16-C17 | -108.1(3) | -111.4(3) |

FIGURE 3

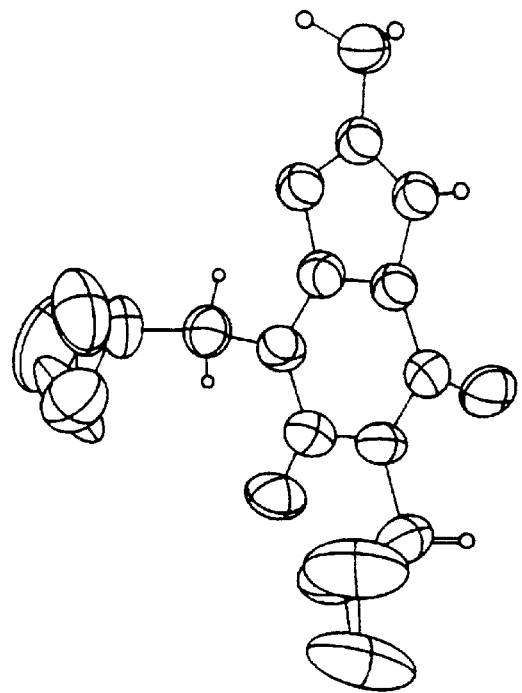
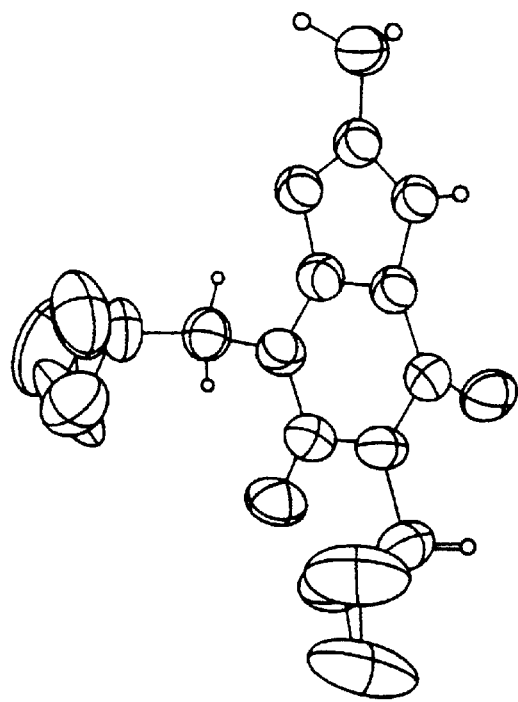
FIG. 11

TABLE OF BOND DISTANCES IN ANGSTROMS

| Atom 1 | Atom 2 | Distance | Atom 1 | Atom 2 | Distance |
|--------|--------|----------|--------|--------|----------|
| O5 | C5 | 1.237(2) | C10 | C11 | 1.493(3) |
| O7 | C7 | 1.211(2) | C11 | C12B | 1.155(5) |
| N1 | C2 | 1.344(2) | C11 | C12A | 1.481(8) |
| N1 | C9 | 1.367(2) | C11 | C13B | 1.366(9) |
| N2 | C2 | 1.355(2) | C11 | C13A | 1.292(5) |
| N3 | C2 | 1.343(2) | C12B | C12A | 1.287(9) |
| N3 | C4 | 1.397(2) | C12B | C13B | 1.50(1) |
| N6 | C5 | 1.399(2) | C12B | C13B | 1.597(8) |
| N6 | C7 | 1.402(2) | C12A | C13B | 0.55(2) |
| N6 | C14 | 1.476(2) | C12A | C13A | 1.55(1) |
| N8 | C7 | 1.388(2) | C13B | C13A | 1.16(1) |
| N8 | C9 | 1.365(2) | C14 | C15 | 1.492(3) |
| N8 | C10 | 1.461(2) | C15 | C16 | 1.453(3) |
| C4 | C5 | 1.407(2) | C15 | C17 | 1.490(3) |
| C4 | C9 | 1.362(2) | C16 | C17 | 1.501(4) |

Numbers in parentheses are estimated standard deviations in the least significant digits.

FIGURE 12

TABLE OF BOND ANGLES IN DEGREES

| Atom 1 | Atom 2 | Atom 3 | Angle | Atom 1 | Atom 2 | Atom 3 | Angle |
|---|---|---|---|---|---|---|---|
| C2 | N1 | C9 | 102.5(1) | C10 | C11 | C12A | 124.9(4) |
| C2 | N3 | C4 | 105.6(1) | C10 | C11 | C13B | 121.6(5) |
| C5 | N6 | C7 | 126.1(1) | C10 | C11 | C13A | 132.1(5) |
| C5 | N6 | C14 | 119.0(1) | C12B | C11 | C12A | 56.9(4) |
| C7 | N6 | C14 | 114.8(1) | C12B | C11 | C13B | 72.5(5) |
| C7 | N8 | C9 | 119.4(1) | C12B | C11 | C13A | 81.3(4) |
| C7 | N8 | C10 | 119.4(1) | C12A | C11 | C13B | 21.6(7) |
| C9 | N8 | C10 | 121.2(1) | C12A | C11 | C13A | 67.8(6) |
| N1 | C2 | N2 | 122.8(1) | C13B | C11 | C13A | 51.6(6) |
| N1 | C2 | N3 | 114.1(1) | C11 | C12B | C12A | 74.5(5) |
| N2 | C2 | N3 | 123.0(1) | C11 | C12B | C13B | 60.3(4) |
| N3 | C4 | C5 | 131.5(1) | C11 | C12B | C13A | 53.1(3) |
| N3 | C4 | C9 | 105.1(1) | C12A | C12B | C13B | 20.9(7) |
| C5 | C4 | C9 | 123.3(1) | C12A | C12B | C13A | 64.1(6) |
| O5 | C5 | N6 | 120.7(1) | C13B | C12B | C13A | 43.8(5) |
| O5 | C5 | C4 | 126.9(1) | C11 | C12A | C12B | 48.7(4) |
| N6 | C5 | C4 | 112.4(1) | C11 | C12A | C13B | 67.(1) |
| O7 | C7 | N6 | 121.5(2) | C11 | C12A | C13A | 50.3(4) |
| O7 | C7 | N8 | 121.6(1) | C12B | C12A | C13B | 102.(2) |
| N6 | C7 | N8 | 116.8(2) | C12B | C12A | C13A | 67.7(5) |
| N1 | C9 | N8 | 125.4(1) | C13B | C12A | C13A | 36.(2) |
| N1 | C9 | C4 | 112.7(2) | C11 | C13B | C12B | 47.2(4) |
| N8 | C9 | C4 | 121.9(1) | C11 | C13B | C12A | 91.(2) |
| N8 | C10 | C11 | 113.6(2) | C11 | C13B | C13A | 60.9(6) |
| C10 | C11 | C12B | 146.4(4) | C12B | C13B | C12A | 57.(1) |
| C12B | C13B | C13A | 72.5(9) | C12A | C13A | C13B | 16.2(7) |
| C12A | C13B | C13A | 127.(2) | N6 | C14 | C15 | 111.7(2) |
| C11 | C13A | C12B | 45.6(3) | C14 | C15 | C16 | 122.2(2) |
| C11 | C13A | C12A | 61.9(4) | C14 | C15 | C17 | 119.2(2) |
| C11 | C13A | C13B | 67.5(5) | C16 | C15 | C17 | 61.3(2) |
| C12B | C13A | C12A | 48.2(4) | C15 | C16 | C17 | 60.6(2) |
| C12B | C13A | C13B | 63.6(6) | C15 | C17 | C16 | 58.1(1) |

Numbers in parenthesis are estimated standard deviations in the least significant digits.

FIGURE 13

TABLE OF TORSION ANGLES IN DEGREES

| Atom 1 | Atom 2 | Atom 3 | Atom 4 | Angle |
|---|---|---|---|---|
| C9 | N1 | C2 | N2 | 178.39(0.21) |
| C9 | N1 | C2 | N3 | 0.00(0.63) |
| C2 | N1 | C9 | N8 | 179.65(0.20) |
| C2 | N1 | C9 | C4 | 0.07(0.22) |
| H1N2 | N2 | C2 | N1 | 17.67(1.50) |
| H1N2 | N2 | C2 | N3 | -164.06(1.48) |
| H2N2 | N2 | C2 | N1 | 165.33(2.43) |
| H2N2 | N2 | C2 | N3 | -16.40(2.45) |
| C4 | N3 | C2 | N1 | -0.04(0.22) |
| C4 | N3 | C2 | N2 | -178.45(0.21) |
| HN3 | N3 | C2 | N1 | -173.47(0.22) |
| HN3 | N3 | C2 | N2 | 8.13(0.40) |
| C2 | N3 | C4 | C5 | -176.94(0.24) |
| C2 | N3 | C4 | C9 | 0.09(0.25) |
| HN3 | N3 | C4 | C5 | -2.31(0.36) |
| HN3 | N3 | C4 | C9 | 174.71(0.19) |
| C7 | N6 | C5 | O5 | 178.56(0.21) |
| C7 | N6 | C5 | C4 | -1.17(0.31) |
| C14 | N6 | C5 | O5 | 3.23(0.32) |
| C14 | N6 | C5 | C4 | -176.50(0.20) |
| C5 | N6 | C7 | O7 | 179.08(0.22) |
| C5 | N6 | C7 | N8 | -0.03(0.30) |
| C14 | N6 | C7 | O7 | -5.42(0.32) |
| C14 | N6 | C7 | N8 | 175.47(0.20) |
| C5 | N6 | C14 | C15 | 97.41(0.27) |
| C7 | N6 | C14 | C15 | -78.43(0.27) |
| C9 | N8 | C7 | O7 | -178.90(0.21) |
| C9 | N8 | C7 | N6 | 0.21(0.31) |
| C10 | N8 | C7 | O7 | 2.31(0.33) |
| C10 | N8 | C7 | N6 | -178.58(0.19) |
| C7 | N8 | C9 | N1 | -178.60(0.20) |
| C7 | N8 | C9 | C4 | 0.94(0.31) |

FIG. 14A

TABLE OF TORSION ANGLES IN DEGREES

| Atom 1 | Atom 2 | Atom 3 | Atom 4 | Angle |
|--------|--------|--------|--------|-------|
| C10 | N8 | C9 | N1 | 0.17(0.34) |
| C10 | N8 | C9 | C4 | 179.71(0.20) |
| C7 | N8 | C10 | C11 | 92.91(0.28) |
| C9 | N8 | C10 | C11 | -85.86(0.29) |
| N3 | C4 | C5 | O5 | -0.82(0.42) |
| N3 | C4 | C5 | N6 | 178.89(0.22) |
| C9 | C4 | C5 | O5 | -177.38(0.22) |
| C9 | C4 | C5 | N6 | 2.33(0.32) |
| N3 | C4 | C9 | N1 | -0.10(0.27) |
| N3 | C4 | C9 | N8 | -179.69(0.20) |
| C5 | C4 | C9 | N1 | 177.23(0.20) |
| C5 | C4 | C9 | N8 | -2.36(0.34) |
| N8 | C10 | C11 | C12B | 18.14(1.01) |
| N8 | C10 | C11 | C12A | -62.89(0.57) |
| N8 | C10 | C11 | C13B | -88.53(0.62) |
| N8 | C10 | C11 | C13A | -153.29(0.60) |
| C10 | C11 | C12B | C12A | -104.52(0.89) |
| C10 | C11 | C12B | C13B | -121.16(0.96) |
| C10 | C11 | C12B | C13A | -173.58(0.98) |
| C12A | C11 | C12B | C13B | -16.64(0.63) |
| C12A | C11 | C12B | C13A | -69.05(0.61) |
| C13B | C11 | C12B | C12A | 16.64(0.63) |
| C13B | C11 | C12B | C13A | -52.42(0.66) |
| C13A | C11 | C12B | C12A | 69.05(0.61) |
| C13A | C11 | C12B | C13B | 52.42(0.66) |
| C10 | C11 | C12A | C12B | 139.20(0.69) |
| C10 | C11 | C12A | C13B | -88.56(1.41) |
| C10 | C11 | C12A | C13A | -126.69(0.69) |
| C12B | C11 | C12A | C13B | 132.25(1.54) |
| C12B | C11 | C12A | C13A | 94.12(0.79) |
| C13B | C11 | C12A | C12B | -132.25(1.54) |
| C13B | C11 | C12A | C13A | -38.13(1.41) |
| C13A | C11 | C12A | C12B | -94.12(0.79) |
| C13A | C11 | C12A | C13B | 38.13(1.41) |
| C10 | C11 | C13B | C12B | 146.19(0.63) |
| C10 | C11 | C13B | C12A | 105.66(1.27) |
| C10 | C11 | C13B | C13A | -121.12(0.76) |

FIG. 14B

TABLE OF TORSION ANGLES IN DEGREES

| Atom 1 | Atom 2 | Atom 3 | Atom 4 | Angle |
|--------|--------|--------|--------|-------|
| C12B | C11 | C13B | C12A | -40.53(1.33) |
| C12B | C11 | C13B | C13A | 92.69(0.84) |
| C12A | C11 | C13B | C12B | 40.53(1.33) |
| C12A | C11 | C13B | C13A | 133.22(1.59) |
| C13A | C11 | C13B | C12B | -92.69(0.84) |
| C13A | C11 | C13B | C12A | -133.22(1.59) |
| C10 | C11 | C13A | C12B | 175.21(0.72) |
| C10 | C11 | C13A | C12A | 117.55(0.63) |
| C10 | C11 | C13A | C13B | 100.66(0.71) |
| C12B | C11 | C13A | C12A | -57.66(0.60) |
| C12B | C11 | C13A | C13B | -74.55(0.70) |
| C12A | C11 | C13A | C12B | 57.66(0.60) |
| C12A | C11 | C13A | C13B | -16.88(0.58) |
| C13B | C11 | C13A | C12B | 74.55(0.60) |
| C13B | C11 | C13A | C12A | 16.88(0.58) |
| C11 | C12B | C12A | C13B | -44.29(1.28) |
| C11 | C12B | C12A | C13A | -56.10(0.52) |
| C13B | C12B | C12A | C11 | 44.29(1.28) |
| C13B | C12B | C12A | C13A | -11.81(1.22) |
| C13A | C12B | C12A | C11 | 56.10(0.52) |
| C13A | C12B | C12A | C13B | 11.81(1.22) |
| C11 | C12B | C13B | C12A | 129.22(1.48) |
| C11 | C12B | C13B | C13A | -66.21(0.66) |
| C12A | C12B | C13B | C11 | -129.22(1.48) |
| C12A | C12B | C13B | C13A | 164.57(1.56) |
| C13A | C12B | C13B | C11 | 66.21(0.66) |
| C13A | C12B | C13B | C12A | -164.57(1.56) |
| C11 | C12B | C13A | C12A | 89.52(0.65) |
| C11 | C12B | C13A | C13B | 83.48(0.69) |
| C12A | C12B | C13A | C11 | -89.52(0.65) |
| C12A | C12B | C13A | C13B | -6.04(0.58) |
| C13B | C12B | C13A | C11 | -83.48(0.69) |
| C13B | C12B | C13A | C12A | 6.04(0.58) |
| C11 | C12A | C13B | C12B | -34.66(0.89) |
| C11 | C12A | C13B | C13A | -53.29(1.16) |
| C12B | C12A | C13B | C11 | 34.66(0.89) |
| C12B | C12A | C13B | C13A | -18.63(1.76) |

FIG. 14C

TABLE OF TORSION ANGLES IN DEGREES

| Atom 1 | Atom 2 | Atom 3 | Atom 4 | Angle |
|--------|--------|--------|--------|-------|
| C13A | C12A | C13B | C12B | 18.63(1.76) |
| C11 | C12A | C13A | C12B | -54.08(0.56) |
| C11 | C12A | C13A | C13B | 106.19(1.75) |
| C12B | C12A | C13A | C11 | 54.08(0.56) |
| C12B | C12A | C13A | C13B | 160.27(1.86) |
| C13B | C12A | C13A | C11 | -106.19(1.75) |
| C13B | C12A | C13A | C12B | -160.27(1.86) |
| C11 | C13B | C13A | C12B | -50.23(0.48) |
| C11 | C13B | C13A | C12A | -66.54(1.64) |
| C12B | C13B | C13A | C11 | 50.23(0.48) |
| C12B | C13B | C13A | C12A | -16.31(1.55) |
| C12A | C13B | C13A | C11 | 66.54(1.64) |
| C12A | C13B | C13A | C12B | 16.31(1.55) |
| N6 | C14 | C15 | C16 | -160.25(0.31) |
| N6 | C14 | C15 | C17 | -87.61(0.35) |
| C14 | C15 | C16 | C17 | 108.17(0.40) |
| C14 | C15 | C17 | C16 | -112.98(0.37) |

FIG. 14D

Positional Parameters and Their Estimated Standard Deviations

| Atom | X | Y | Z | B(A2) |
|---|---|---|---|---|
| O5 | 1.5599(1) | 1.8918(1) | 1.1475(3) | 4.88(4) |
| O7 | 1.3047(2) | 1.7197(1) | 0.5279(3) | 5.25(4) |
| N1 | 1.1341(2) | 1.9527(1) | 1.2713(4) | 3.77(4) |
| N2 | 1.1397(2) | 2.0771(2) | 1.6721(4) | 4.71(4) |
| N3 | 1.3206(2) | 1.9967(1) | 1.4356(4) | 3.89(4) |
| N6 | 1.4311(2) | 1.8063(2) | 0.8378.(4) | 4.13(4) |
| N8 | 1.2113(2) | 1.8305(1) | 0.8786.(4) | 3.90(4) |
| C2 | 1.1968(2) | 2.0099(2) | 1.4663(4) | 3.70(4) |
| C4 | 1.3420(2) | 1.9242(2) | 1.1994(4) | 3.83(4) |
| C5 | 1.4528(2) | 1.8769(2) | 1.0720(5) | 3.94(5) |
| C7 | 1.3146(2) | 1.7809(2) | 0.7346(5) | 4.11(5) |
| C9 | 1.2273(2) | 1.9003(2) | 1.1082(4) | 3.57(4) |
| C10 | 1.0876(2) | 1.8054(2) | 0.7843(5) | 4.60(5) |
| C11 | 1.0417(3) | 1.7161(3) | 0.9008(9) | 8.42(9) |
| C12B | 1.0527(8) | 1.6649(6) | 1.069(2) | 10.7(2) |
| C12A | 1.1006(7) | 1.6034(5) | 0.863(2) | 9.9(2) |
| C13B | 1.066(1) | 1.6107(5) | 0.786(2) | 11.4(3) |
| C13A | 0.9638(6) | 1.6475(8) | 0.814(2) | 12.2(3) |
| C14 | 1.5381(2) | 1.7453(2) | 0.6891(5) | 5.12(6) |
| C15 | 1.5630(3) | 1.6339(3) | 0.7530(7) | 7.89(9) |
| C16 | 1.6823(4) | 1.5701(4) | 0.7024(9) | 11.2(1) |
| C17 | 1.6453(4) | 1.6152(4) | 0.9832(9) | 10.9(1) |

Anisotropically refined atoms are given in the form of the isotropic equivalent displacement parameter defined as: $(4/3) * [a^2 * B(1,1) + b^2 * B(2,2) + c^2 * B(3,3) + ab(\cos \gamma) * B(1,2) + ac(\cos \beta) * B(1,3) + bc(\cos \alpha) + B(2,3)]$

FIGURE 15

TABLE OF BOND DISTANCES IN ANGSTROMS

| Atom 1 | Atom 2 | Distance | Atom 1 | Atom 2 | Distance | Atom 1 | Atom 2 | Distance |
|---|---|---|---|---|---|---|---|---|
| O5 | C5 | 1.243(2) | N6 | C7 | 1.396(2) | C11 | C12 | 1.480(4) |
| O7 | C7 | 1.214(2) | N6 | C14 | 1.477(2) | C11 | C13 | 1.468(3) |
| N1 | C2 | 1.335(2) | N8 | C7 | 1.390(2) | C12 | C13 | 1.457(3) |
| N1 | C9 | 1.367(2) | N8 | C9 | 1.362(2) | C14 | C15 | 1.494(3) |
| N2 | C2 | 1.351(2) | N8 | C10 | 1.475(2) | C15 | C16 | 1.478(4) |
| N3 | C2 | 1.345(2) | C4 | C5 | 1.412(2) | C15 | C17 | 1.487(3) |
| N3 | C4 | 1.391(2) | C4 | C9 | 1.358(2) | C16 | C17 | 1.467(3) |
| N6 | C5 | 1.398(2) | C10 | C11 | 1.494(3) | | | |

Numbers in parentheses are estimated standard deviations in the least significant digits.

FIGURE 28

TABLE OF BOND ANGLES IN DEGREES

| Atom 1 | Atom 2 | Atom 3 | Angle    | Atom 1 | Atom 2 | Atom 3 | Angle    | Atom 1 | Atom 2 | Atom 3 | Angle    |
|--------|--------|--------|----------|--------|--------|--------|----------|--------|--------|--------|----------|
| C2     | N1     | C9     | 103.0(1) | N3     | C4     | C9     | 105.3(1) | C10    | C11    | C12    | 118.9(2) |
| C2     | N3     | C4     | 105.8(1) | C5     | C4     | C9     | 123.2(2) | C10    | C11    | C13    | 120.6(2) |
| C2     | N6     | C7     | 126.3(1) | O5     | C5     | N6     | 121.2(1) | C12    | C11    | C13    | 59.2(2)  |
| C5     | N6     | C14    | 117.7(1) | O5     | C5     | C4     | 126.5(2) | C11    | C12    | C13    | 60.0(2)  |
| C7     | N6     | C14    | 115.9(1) | N6     | C5     | C4     | 112.2(1) | C11    | C13    | C12    | 60.8(2)  |
| C7     | N8     | C9     | 119.7(1) | O7     | C7     | N6     | 122.4(2) | C13    | C14    | C15    | 112.3(2) |
| C7     | N8     | C10    | 117.6(1) | O7     | C7     | N8     | 121.0(2) | C14    | C15    | C16    | 121.2(2) |
| C9     | N8     | C10    | 122.4(1) | N6     | C7     | N8     | 116.6(1) | C14    | C15    | C17    | 118.3(2) |
| N1     | C2     | N2     | 124.2(2) | N1     | C9     | N8     | 125.9(1) | C16    | C15    | C17    | 59.3(2)  |
| N1     | C2     | N3     | 113.7(1) | N1     | C9     | C4     | 112.3(1) | C15    | C16    | C17    | 60.6(2)  |
| N2     | C2     | N3     | 122.1(2) | N8     | C9     | C4     | 121.8(1) | C15    | C17    | C16    | 60.0(2)  |
| N3     | C4     | C5     | 131.3(2) | N8     | C10    | C11    | 112.0(2) |        |        |        |          |

Numbers in parentheses are estimated standard deviations in the least significant digits.

FIGURE 29

TABLE OF TORSIONAL ANGLES IN DEGREES

| Atom 1 | Atom 2 | Atom 3 | Atom 4 | Angle | Atom 1 | Atom 2 | Atom 3 | Atom 4 | Angle |
|---|---|---|---|---|---|---|---|---|---|
| C9 | N1 | C2 | N2 | 179.22(0.22) | N3 | C4 | C9 | N8 | -178.86(0.19) |
| C9 | N1 | C2 | N3 | 0.77(0.25) | C5 | C4 | C9 | N1 | 176.60(0.20) |
| C9 | N1 | C2 | N8 | 178.50(0.21) | C5 | C4 | C9 | N8 | -2.61(0.34) |
| C2 | N1 | C9 | C4 | -0.68(0.24) | N8 | C10 | C11 | C12 | 80.44(0.32) |
| C2 | N1 | C9 | N1 | 167.56(2.15) | N8 | C10 | C11 | C13 | 149.79(0.27) |
| H1N2 | N2 | C2 | N1 | -14.11(2.17) | N8 | C10 | C11 | HC11 | 4.32(2.94) |
| H1N2 | N2 | C2 | N3 | 11.84(1.96) | H1C10 | C10 | C11 | C12 | -159.31(2.98) |
| H2N2 | N2 | C2 | N1 | -169.83(1.93) | H1C10 | C10 | C11 | C13 | -89.96(2.98) |
| H2N2 | N2 | C2 | N3 | -0.59(0.26) | H1C10 | C10 | C11 | HC11 | 124.57(4.16) |
| C4 | N3 | C2 | N1 | -179.07(0.21) | C10 | C11 | C12 | C13 | 110.38(0.32) |
| C4 | N3 | C2 | N2 | -177.62(1.77) | C10 | C11 | C12 | HC11 | -147.35(1.63) |
| HN3 | N3 | C2 | N1 | 3.89(1.79) | C13 | C11 | C12 | HC11 | -1.59(0.50) |
| HN3 | N3 | C2 | N2 | -175.70(0.23) | C13 | C11 | C12 | HC11 | 102.26(1.61) |
| C2 | N3 | C4 | C5 | 0.13(0.23) | HC11 | C11 | C12 | H1C13 | -111.98(0.40) |
| C2 | N3 | C4 | C9 | 0.78(2.14) | HC11 | C11 | C12 | H1C13 | -102.26(1.61) |
| HN3 | N3 | C4 | C5 | 176.60(2.11) | C10 | C11 | C13 | H1C13 | 145.76(1.64) |
| HN3 | N3 | C4 | C9 | 178.11(0.21) | C12 | C11 | C13 | C12 | -107.50(0.33) |
| C7 | N6 | C5 | O5 | -1.77(0.31) | HC11 | C11 | C13 | H1C12 | 141.23(0.31) |
| C7 | N6 | C5 | C4 | 1.69(0.31) | HC11 | C11 | C13 | H1C12 | -111.28(0.38) |
| C14 | N6 | C5 | O5 | -178.19(0.19) | HC1 | C11 | C13 | C12 | 56.85(1.39) |
| C14 | N6 | C5 | C4 | 179.80(0.22) | HC1 | C11 | C13 | H1C12 | -54.43(1.41) |
| C5 | N6 | C7 | O7 | -0.20(0.32) | C10 | C11 | HC11 | C12 | 92.91(2.68) |
| C5 | N6 | C7 | N8 | | | | | | |

FIG. 30A

TABLE OF TORSIONAL ANGLES IN DEGREES

| Atom 1 | Atom 2 | Atom 3 | Atom 4 | Angle | Atom 1 | Atom 2 | Atom 3 | Atom 4 | Angle |
|---|---|---|---|---|---|---|---|---|---|
| C14 | N6 | C7 | O7 | -3.72(0.32) | C13 | C11 | HC11 | C12 | -57.68(0.80) |
| C14 | N6 | C7 | N8 | 176.29(0.19) | C11 | C12 | C13 | HC11 | 109.36(0.36) |
| C5 | N6 | C14 | C15 | 91.67(0.25) | HC11 | C12 | C13 | C11 | -45.77(1.19) |
| C5 | N6 | C14 | H1C14 | -150.04(2.73) | HC11 | C12 | C13 | H1C12 | 63.59(1.22) |
| C5 | N6 | C14 | C15 | -85.13(0.26) | H1C13 | C12 | C13 | C11 | 108.50(0.41) |
| C5 | N6 | C14 | H1C14 | 33.16(2.74) | H1C13 | C12 | C13 | H1C12 | -142.15(0.36) |
| C7 | N8 | C9 | O7 | -178.99(0.21) | C13 | C12 | C13 | C11 | 60.10(1.04) |
| C9 | N8 | C7 | N6 | 1.01(0.30) | H1C13 | C12 | C13 | HC11 | -73.54(2.58) |
| C10 | N8 | C7 | O7 | 6.73(0.32) | N6 | C14 | C15 | C16 | 89.36(0.32) |
| C10 | N8 | C7 | N6 | -173.28(0.19) | N6 | C14 | C15 | C17 | 158.79(0.25) |
| C7 | N8 | C9 | N1 | -178.77(0.21) | N6 | C14 | C15 | HC15 | -53.54(2.68) |
| C7 | N8 | C9 | C4 | 0.33(0.32) | H1C14 | C14 | C15 | C16 | -26.61(2.79) |
| C10 | N8 | C9 | N1 | -4.78(0.34) | H1C14 | C14 | C15 | C17 | 42.82(2.78) |
| C10 | N8 | C9 | C4 | 174.32(0.21) | H1C14 | C14 | C15 | HC15 | -169.51(3.84) |
| C7 | N8 | C10 | C11 | 74.61(0.27) | C14 | C15 | C16 | C17 | 106.62(0.32) |
| C7 | N8 | C10 | H1C10 | -50.49(2.79) | HC15 | C15 | C16 | C17 | -104.94(2.34) |
| C9 | N8 | C10 | C11 | -99.51(0.26) | C14 | C15 | C17 | C16 | -111.35(0.32) |
| C9 | N8 | C10 | H1C10 | 135.39(2.79) | C16 | C15 | C17 | HC15 | 139.79(0.30) |
| N3 | C4 | C5 | O5 | -1.55(0.40) | HC15 | C15 | C16 | C17 | -108.85(0.37) |
| N3 | C4 | C5 | N6 | 178.32(0.21) | HC15 | C15 | C17 | C16 | 97.10(2.41) |
| C9 | C4 | C5 | O5 | -176.73(0.22) | C15 | C16 | C17 | H1C16 | -11.75(2.43) |
| C9 | C4 | C5 | N6 | 3.14(0.31) | H1C16 | C16 | C17 | H1C16 | 110.17(0.40) |
| N3 | C4 | C9 | N1 | 0.35(0.25) | | | | | |

FIG. 30B

POSITIONAL PARAMETERS AND THEIR ESTIMATED STANDARD DEVIATIONS

| ATOM | X | Y | Z | B(A2) |
|---|---|---|---|---|
| O5  | 0.1193(2)  | 0.8847(1) | 0.7643(3)  | 4.17(4) |
| O7  | -0.0432(2) | 0.7070(1) | -0.0448(3) | 4.94(4) |
| N1  | -0.3270(2) | 0.9413(1) | 0.4337(4)  | 3.61(4) |
| N2  | -0.3813(2) | 1.0649(2) | 0.7969(5)  | 5.08(5) |
| N3  | 0.1646(2)  | 0.9868(1) | 0.7668(4)  | 3.62(4) |
| N6  | 0.0374(2)  | 0.7967(1) | 0.3570(4)  | 3.69(4) |
| N8  | 0.1894(2)  | 0.8182(1) | 0.1688(4)  | 3.63(4) |
| C2  | 0.2944(2)  | 0.9987(2) | 0.6689(5)  | 3.68(5) |
| C4  | 0.1072(2)  | 0.9147(2) | 0.5811(5)  | 3.48(5) |
| C5  | 0.0236(2)  | 0.8679(2) | 0.5850(5)  | 3.42(5) |
| C7  | 0.0633(2)  | 0.7697(2) | 0.1476(5)  | 3.83(5) |
| C9  | 0.2085(2)  | 0.8891(2) | 0.3845(5)  | 3.33(4) |
| C10 | 0.3002(2)  | 0.7832(2) | -0.0323(5) | 4.21(5) |
| C11 | -0.3407(3) | 0.6883(2) | 0.0279(7)  | 5.89(7) |
| C12 | -0.4282(4) | 0.6908(3) | 0.2439(8)  | 7.09(9) |
| C13 | -0.4789(3) | 0.6647(2) | -0.0445(7) | 6.82(8) |
| C14 | 0.1687(2)  | 0.7401(2) | 0.3404(5)  | 4.33(5) |
| C15 | 0.1807(3)  | 0.6467(2) | 0.4687(6)  | 5.81(7) |
| C16 | 0.1415(3)  | 0.5538(2) | 0.3060(9)  | 7.6(1) |
| C17 | 0.2830(3)  | 0.5663(2) | 0.3858(8)  | 6.86(9) |

Anisotropically refined atoms are given in the form of the isotropic equivalent displacement parameter defined as: $(4/3) * [a^2*B(1,1) + b^2*B(2,2) + c^2*B(3,3) + ab(\cos \gamma)*B(1,2) + ac(\cos \beta)*B(1,3) + bc(\cos \alpha)*B(2,3)]$

FIGURE 31

TABLE OF BOND DISTANCES IN ANGSTROMS

| Atom 1 | Atom 2 | Distance | Atom 1 | Atom 2 | Distance |
|---|---|---|---|---|---|
| O5 | C5 | 1.251(3) | N8 | C10 | 1.485(3) |
| O7 | C7 | 1.216(3) | C4 | C5 | 1.386(3) |
| N1 | C2 | 1.352(3) | C4 | C9 | 1.368(3) |
| N1 | C9 | 1.351(3) | C10 | C11 | 1.494(4) |
| N2 | C2 | 1.344(3) | C11 | C12 | 1.493(4) |
| N3 | C2 | 1.340(3) | C11 | C13 | 1.509(4) |
| N3 | C4 | 1.394(3) | C12 | C13 | 1.513(5) |
| N6 | C5 | 1.402(3) | C14 | C15 | 1.496(4) |
| N6 | C7 | 1.403(3) | C15 | C16 | 1.498(4) |
| N6 | C14 | 1.474(3) | C15 | C17 | 1.491(4) |
| N8 | C7 | 1.375(3) | C16 | C17 | 1.497(4) |
| N8 | C9 | 1.375(3) | | | |

Numbers in parentheses are estimated standard deviations in the least significant digits.

FIGURE 33

TABLE OF BOND ANGLES IN DEGREES

| Atom 1 | Atom 2 | Atom 3 | Angle | Atom 1 | Atom 2 | Atom 3 | Angle |
|---|---|---|---|---|---|---|---|
| C2 | N1 | C9 | 102.9(2) | O7 | C7 | N8 | 122.2(2) |
| C2 | N3 | C4 | 106.5(2) | N6 | C7 | N8 | 117.1(2) |
| C5 | N6 | C7 | 125.4(2) | N1 | C9 | N8 | 125.6(2) |
| C5 | N6 | C14 | 119.4(2) | N1 | C9 | C4 | 113.2(2) |
| C7 | N6 | C14 | 115.3(2) | N8 | C9 | C4 | 121.2(2) |
| C7 | N8 | C9 | 119.7(2) | N8 | C10 | C11 | 113.2(2) |
| C7 | N8 | C10 | 119.0(2) | C10 | C11 | C12 | 118.9(3) |
| C9 | N8 | C10 | 121.0(2) | C10 | C11 | C13 | 115.7(3) |
| N1 | C2 | N2 | 122.6(2) | C12 | C11 | C13 | 60.5(2) |
| N1 | C2 | N3 | 113.2(2) | C11 | C12 | C13 | 60.3(2) |
| N2 | C2 | N3 | 124.2(2) | C11 | C13 | C12 | 59.2(2) |
| N3 | C4 | C5 | 132.3(2) | N6 | C14 | C15 | 111.5(2) |
| N3 | C4 | C9 | 104.3(2) | C14 | C15 | C16 | 119.3(2) |
| C5 | C4 | C9 | 123.4(2) | C14 | C15 | C17 | 118.6(3) |
| O5 | C5 | N6 | 120.1(2) | C16 | C15 | C17 | 60.1(2) |
| O5 | C5 | C4 | 126.7(2) | C15 | C16 | C17 | 59.7(2) |
| N6 | C5 | C4 | 113.2(2) | C15 | C17 | C16 | 60.2(2) |
| O7 | C7 | N6 | 120.7(2) | | | | |

Numbers in parentheses are estimated standard deviations in the least significant digits.

FIGURE 34

TABLE OF TORSION ANGLES IN DEGREES

| Atom 1 | Atom 2 | Atom 3 | Atom 4 | Angle |
|--------|--------|--------|--------|-------|
| C9 | N1 | C2 | N2 | 178.05(0.24) |
| C9 | N1 | C2 | N3 | 0.08(0.30) |
| C2 | N1 | C9 | N8 | -177.92(0.24) |
| C2 | N1 | C9 | C4 | 0.10(0.28) |
| H1N2 | N2 | C2 | N1 | 23.12(2.03) |
| H1N2 | N2 | C2 | N3 | -159.14(2.01) |
| H2N2 | N2 | C2 | N1 | 168.86(2.37) |
| H2N2 | N2 | C2 | N3 | -13.40(2.39) |
| C4 | N3 | C2 | N1 | -0.23(0.28) |
| C4 | N3 | C2 | N2 | -178.15(0.24) |
| HN3 | N3 | C2 | N1 | -179.38(2.06) |
| HN3 | N3 | C2 | N2 | 2.70(2.09) |
| C2 | N3 | C4 | C5 | 178.30(0.28) |
| C2 | N3 | C4 | C9 | 0.27(0.26) |
| HN3 | N3 | C4 | C5 | -2.56(2.13) |
| HN3 | N3 | C4 | C9 | 179.41(2.09) |
| C7 | N6 | C5 | O5 | -176.21(0.23) |
| C7 | N6 | C5 | C4 | 4.06(0.35) |
| C14 | N6 | C5 | O5 | 5.06(0.35) |
| C14 | N6 | C5 | C4 | -174.67(0.22) |
| C5 | N6 | C7 | O7 | 178.07(0.24) |
| C5 | N6 | C7 | N8 | -1.50(0.37) |
| C14 | N6 | C7 | O7 | -3.15(0.36) |
| C14 | N6 | C7 | N8 | 177.28(0.22) |
| C5 | N6 | C14 | C15 | 98.71(0.28) |
| C5 | N6 | C14 | H1C14 | -23.62(1.66) |
| C5 | N6 | C14 | H2C14 | -139.30(1.34) |
| C7 | N6 | C14 | C15 | -80.15(0.29) |
| C7 | N6 | C14 | H1C14 | 157.52(1.64) |
| C7 | N6 | C14 | H2C14 | 41.84(1.36) |
| C9 | N8 | C7 | O7 | 178.13(0.25) |
| C9 | N8 | C7 | N6 | -2.30(0.35) |
| C10 | N8 | C7 | O7 | -8.17(0.38) |
| C10 | N8 | C7 | N6 | 171.39(0.22) |
| C7 | N8 | C9 | N1 | -178.88(0.24) |
| C7 | N8 | C9 | C4 | 3.26(0.36) |

FIG. 35A

TABLE OF TORSION ANGLES IN DEGREES

| Atom 1 | Atom 2 | Atom 3 | Atom 4 | Angle |
|---|---|---|---|---|
| C10 | N8 | C9 | N1 | 7.55(0.38) |
| C10 | N8 | C9 | C4 | -170.32(0.24) |
| C7 | N8 | C10 | C11 | 101.83(0.28) |
| C7 | N8 | C10 | H1C10 | -138.74(1.37) |
| C7 | N8 | C10 | H2C10 | -20.54(1.49) |
| C9 | N8 | C10 | C11 | -84.56(0.30) |
| C9 | N8 | C10 | H1C10 | 34.87(1.39) |
| C9 | N8 | C10 | H2C10 | 153.07(1.47) |
| N3 | C4 | C5 | O5 | -0.50(0.47) |
| N3 | C4 | C5 | N6 | 179.21(0.25) |
| C9 | C4 | C5 | O5 | 177.22(0.25) |
| C9 | C4 | C5 | N6 | -3.08(0.36) |
| N3 | C4 | C9 | N1 | -0.23(0.29) |
| N3 | C4 | C9 | N8 | 177.88(0.22) |
| C5 | C4 | C9 | N1 | -178.49(0.23) |
| C5 | C4 | C9 | N8 | -0.38(0.40) |
| N8 | C10 | C11 | C12 | -77.46(0.37) |
| N8 | C10 | C11 | C13 | -146.45(0.28) |
| N8 | C10 | C11 | HC11 | 69.33(2.00) |
| H1C10 | C10 | C11 | C12 | 165.55(1.46) |
| H1C10 | C10 | C11 | C13 | 96.55(1.46) |
| H1C10 | C10 | C11 | HC11 | -47.66(2.46) |
| H2C10 | C10 | C11 | C12 | 38.83(1.63) |
| H2C10 | C10 | C11 | C13 | -30.17(1.63) |
| H2C10 | C10 | C11 | HC11 | -174.38(2.54) |
| C10 | C11 | C12 | C13 | -104.89(0.35) |
| C10 | C11 | C12 | H1C12 | -3.01(2.32) |
| C10 | C11 | C12 | H2C12 | 145.37(2.57) |
| C13 | C11 | C12 | H1C12 | 101.87(2.29) |
| C13 | C11 | C12 | H2C12 | -109.74(2.58) |
| HC11 | C11 | C12 | C13 | 106.38(1.89) |
| HC11 | C11 | C12 | H1C12 | -151.74(2.94) |
| HC11 | C11 | C12 | H2C12 | -3.35(3.20) |
| C10 | C11 | C13 | C12 | 110.08(0.32) |
| C10 | C11 | C13 | H1C13 | -142.62(3.05) |
| C10 | C11 | C13 | H2C13 | -12.37(0.72) |

FIG. 35B

TABLE OF TORSION ANGLES IN DEGREES

| Atom 1 | Atom 2 | Atom 3 | Atom 4 | Angle |
|--------|--------|--------|--------|-------|
| C12 | C11 | C13 | H1C13 | 107.30(3.06) |
| C12 | C11 | C13 | H2C13 | -122.45(0.65) |
| HC11 | C11 | C13 | C12 | -104.01(1.90) |
| HC11 | C11 | C13 | H1C13 | 3.29(3.59) |
| HC11 | C11 | C13 | H2C13 | 133.54(1.94) |
| C11 | C12 | C13 | H1C13 | -95.14(3.19) |
| C11 | C12 | C13 | H2C13 | 130.82(0.53) |
| H1C12 | C12 | C13 | C11 | -106.46(2.08) |
| H1C12 | C12 | C13 | H1C13 | 158.40(3.79) |
| H1C12 | C12 | C13 | H2C13 | 24.36(2.14) |
| H2C12 | C12 | C13 | C11 | 104.58(2.65) |
| H2C12 | C12 | C13 | H1C13 | 9.43(4.15) |
| H2C12 | C12 | C13 | H2C13 | -124.61(2.67) |
| N6 | C14 | C15 | C16 | -88.54(0.33) |
| N6 | C14 | C15 | C17 | -158.33(0.26) |
| N6 | C14 | C15 | HC15 | 63.31(1.86) |
| H1C14 | C14 | C15 | C16 | 31.45(1.66) |
| H1C14 | C14 | C15 | C17 | -38.35(1.65) |
| H1C14 | C14 | C15 | HC15 | -176.71(2.45) |
| H2C14 | C14 | C15 | C16 | 153.51(1.42) |
| H2C14 | C14 | C15 | C17 | 83.71(1.44) |
| H2C14 | C14 | C15 | HC15 | -54.65(2.33) |
| C14 | C15 | C16 | C17 | -108.05(0.32) |
| C14 | C15 | C16 | H1C16 | -0.20(1.73) |
| C14 | C15 | C16 | H2C16 | 144.46(2.42) |
| C17 | C15 | C16 | H1C16 | 107.85(1.72) |
| C17 | C15 | C16 | H2C16 | -107.49(2.43) |
| HC15 | C15 | C16 | C17 | 103.34(2.05) |
| HC15 | C15 | C16 | H1C16 | -148.81(2.65) |
| HC15 | C15 | C16 | H2C16 | -4.15(3.19) |
| C14 | C15 | C17 | C16 | 109.24(0.32) |
| C14 | C15 | C17 | H1C17 | -143.46(2.06) |
| C14 | C15 | C17 | H2C17 | -0.28(2.06) |
| C16 | C15 | C17 | H1C17 | 107.30(2.08) |
| C16 | C15 | C17 | H2C17 | -109.52(2.04) |

FIG. 35C

TABLE OF TORSION ANGLES IN DEGREES

| Atom 1 | Atom 2 | Atom 3 | Atom 4 | Angle |
|--------|--------|--------|--------|-------|
| HC15   | C15    | C17    | C16    | -114.19(2.00) |
| HC15   | C15    | C17    | H1C17  | -6.89(2.88) |
| HC15   | C15    | C17    | H2C17  | 136.29(2.83) |
| C15    | C16    | C17    | H1C17  | -108.70(2.12) |
| C15    | C16    | C17    | H2C17  | 107.42(2.08) |
| H1C16  | C16    | C17    | C15    | -100.24(1.88) |
| H1C16  | C16    | C17    | H1C17  | 151.06(2.81) |
| H1C16  | C16    | C17    | H2C17  | 7.18(2.80) |
| H2C16  | C16    | C17    | C15    | 111.79(2.55) |
| H2C16  | C16    | C17    | H1C17  | 3.09(3.32) |
| H2C16  | C16    | C17    | H2C17  | -140.79(3.27) |

FIG. 35D

POSITIONAL PARAMETERS AND THEIR ESTIMATED STANDARD DEVIATIONS

| ATOM | X | Y | Z | B(A2) |
|---|---|---|---|---|
| O5  | 0.9075(2) | -0.3990(2) | 0.8878(1) | 3.22(4) |
| O7  | 0.7135(2) | 0.1280(3)  | .08696(1) | 3.93(5) |
| N1  | 0.9202(2) | -0.0215(3) | 1.1348(1) | 2.60(5) |
| N2  | 1.0398(2) | -0.1997(3) | 1.2364(2) | 3.35(5) |
| N3  | 0.9771(2) | -0.2857(3) | 1.0851(1) | 2.85(5) |
| N6  | 0.8070(2) | -0.1371(3) | 0.8743(1) | 2.61(5) |
| N8  | 0.8128(2) | 0.0729(3)  | 0.9941(2) | 2.61(5) |
| C2  | 0.9803(2) | -0.1720(4) | 1.1549(2) | 2.58(5) |
| C4  | 0.9096(2) | -0.2061(3) | 1.0131(2) | 2.44(5) |
| C5  | 0.8785(2) | -0.2590(4) | 0.9243(2) | 2.53(5) |
| C7  | 0.7738(2) | 0.0287(4)  | 0.9061(2) | 2.86(6) |
| C9  | 0.8781(2) | -0.0468(3) | 1.0473(2) | 2.33(5) |
| C10 | 0.7932(2) | 0.2569(4)  | 1.0268(2) | 3.20(6) |
| C11 | 0.7010(3) | 0.2660(5)  | 1.0827(2) | 4.22(7) |
| C12 | 0.5848(3) | 0.2621(6)  | 1.0363(3) | 6.2(1)  |
| C13 | 0.6342(3) | 0.4370(5)  | 1.0743(3) | 7.0(1)  |
| C14 | 0.7592(2) | -0.1827(4) | 0.7812(2) | 3.04(6) |
| C15 | 0.6443(2) | -0.2544(4) | 0.7773(2) | 3.73(7) |
| C16 | 0.6275(3) | -0.4518(5) | 0.7891(3) | 5.49(9) |
| C17 | 0.5985(3) | 0.3664(5)  | 0.6983(3) | 5.36(9) |

Anisotropically refined atoms are given in the form of the isotropic equivalent displacement parameter defined as: $(4/3) * [a^2*B(1,1) + b^2*B(2,2) + c^2*B(3,3) + ab(\cos \gamma) *B(1,2) + ac(\cos \beta) *B(1,3) + bc(\cos \alpha) *B(2,3)]$

FIGURE 36

POLYMORPHIC FORMS OF CIPAMFYLLINE

This application claims the benefit of provisional application No. 60/063,238 filed Oct. 23, 1997.

FIELD OF THE INVENTION

This invention relates to novel crystalline polymorphic forms of Cipamfylline, and to methods for preparing them.

BACKGROUND OF THE INVENTION

The capacity to occur in different crystal structures is known as polymorphism and is known to occur in many organic compounds. These different crystalline forms are known as "polymorphic modifications" or "polymorphs" and are realized in their crystalline state. While polymorphic modifications have the same chemical composition, they differ in packing, geometrical arrangement, and other descriptive properties of the crystalline solid state. As such, these modifications may have different solid-state physical properties such as shape, color density, hardness, deformability, stability, and dissolution properties, etc. Polymorphism of an organic drug molecule and its consequences will be appreciated by the skilled artisan.

Cipamfylline, 1,3-di-cyclopropylmethyl-8-amino xanthine, has the chemical formula $C_{13}H_{17}N_5O_2$, m.w. of 275.31, and the following structural formula:

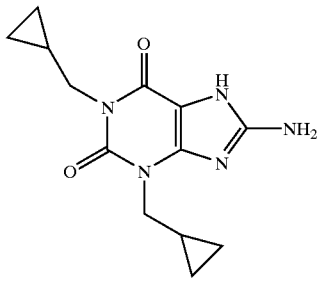

Its synthesis is described in Example 9, in Maschler et al., Great Britain Patent Application No. 8906792.0 filed on Mar. 23, 1989, in its corresponding EPO patent EP 389282, and corresponding U.S. Pat. No. 5,734,051 whose disclosures are incorporated herein by reference in their entirety.

Cipamfylline is a $PDE_4$ inhibitor and is useful in the treatment, including prophylaxis, of disease states mediated thereby.

Cipamfylline was also disclosed to have TNF inhibiting activity in Esser et al., PCT/US91/08734 (also published as EP 558659), and is therefore useful in the treatment, including prophylaxis of TNF mediated disease states. Suitable assays, dosage forms, and dosage ranges, etc. for the polymorphs of this invention for use in the therapeutic treatment of diseases may be found in either the Maschler et al., or the Esser et al. patent applications whose disclosures are incorporated herein by reference in their entirety.

SUMMARY OF THE INVENTION

This invention relates to a novel crystalline polymorph of the 1,3-di-cyclopropylmethyl-8-amino xanthine, referred to hereinafter as Form I, which form of such compound is useful in the treatment of $PDE_4$ or TNF mediated diseases.

This invention also relates to a novel crystalline polymorph of the 1,3-di-cyclopropylmethyl-8-amino xanthine, referred to hereinafter as Form II, which form of such compound is useful in the treatment of $PDE_4$ or TNF mediated diseases.

This invention also relates to a novel crystalline polymorph of the 1,3-di-cyclopropylmethyl-8-amino xanthine, referred to hereinafter as Form IV, which form of such compound is useful in the treatment of $PDE_4$ or TNF mediated diseases.

BRIEF DESCRIPTION OF THE DRAWINGS

FIG. 3 is a table showing the Torsion Angle Tabulations for Forms II and IV.

FIG. 11 provides for a stereo drawing of the Form I molecule.

FIG. 12 shows a Table of Bond Distances in Angstroms for the Form I molecule.

FIG. 13 shows a Table of Bond Angles in Degrees for the Form I molecule.

FIG. 14 shows a Table of Torsion Angles in Degrees for the Form I molecule.

FIG. 15 shows a Table of Positional Parameters and Their Estimated Standard Deviations for the Form I molecule. The x, y, and z fractional coordinates indicate the position of atoms relative to the origin of the unit cell, and B(A2) is the isotropic temperature factor.

FIG. 28 shows a Table of Bond Distances in Angstroms for the Form IV molecule.

FIG. 29 shows a Table of Bond Angles in Degrees for the Form IV molecule.

FIG. 30 shows a Table of Torsion Angles in Degrees for the Form IV molecule.

FIG. 31 shows a Table of Positional Parameters and Their Estimated Standard Deviations for the Form IV molecule.

FIG. 33 shows a Table of Bond Distances in Angstroms for the Form II molecule.

FIG. 34 shows a Table of Bond Angles in Degrees for the Form II molecule.

FIG. 35 shows a Table of Torsion Angles in Degrees for the Form II molecule.

FIG. 36 shows a Table of Positional Parameters and Their Estimated Standard Deviations for the Form II molecule.

DETAILED DESCRIPTION OF THE INVENTION

Figure 1:
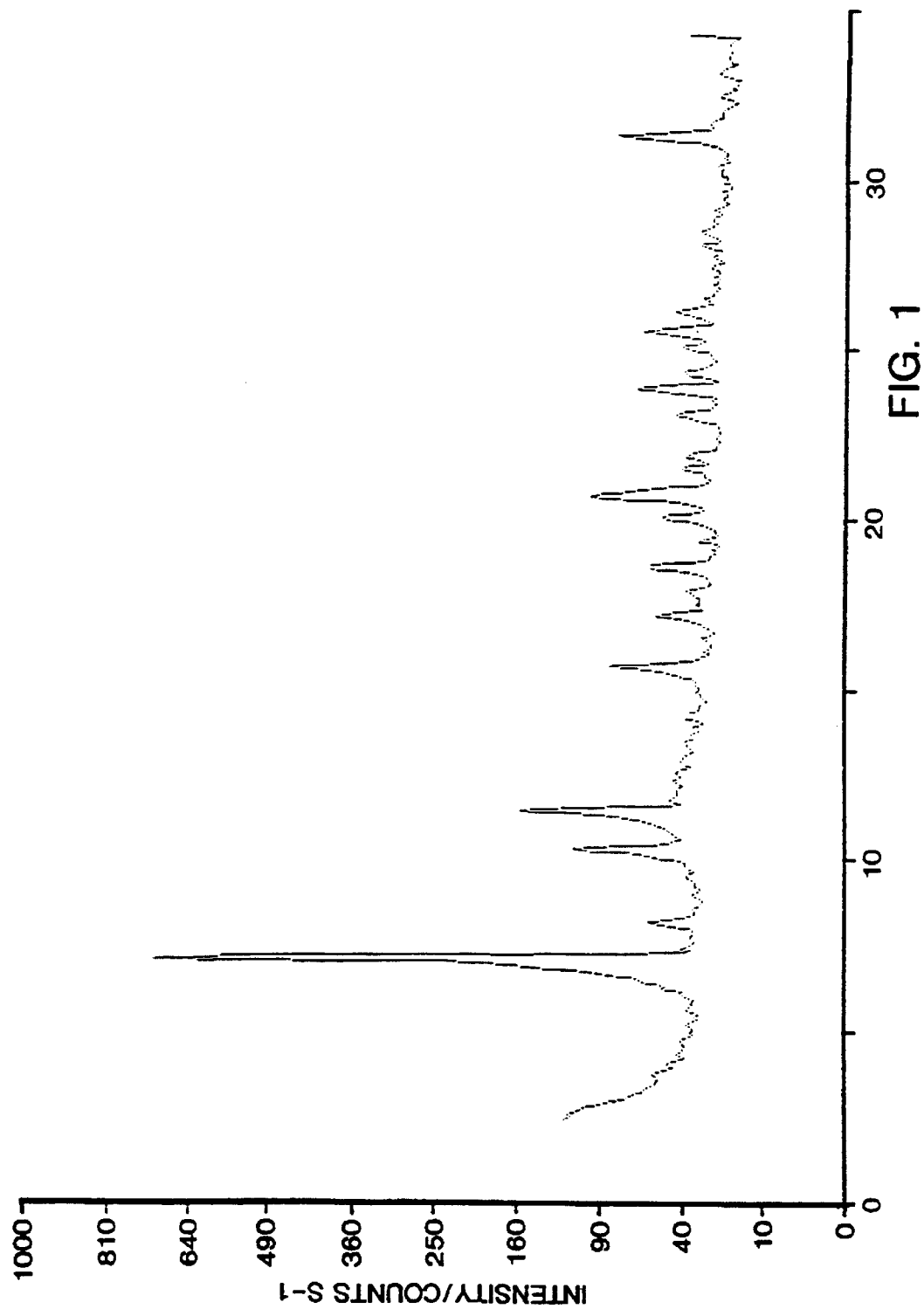
FIG. 1 is a characteristic X-ray powder diffraction pattern for Form I. (Vertical axis: Intensity (CPS); Horizontal axis: Diffraction Angle, in Two Theta (degrees)).

It has now been discovered that Cipamfylline can exist as any of several novel crystalline forms, polymorphic forms, which differ from each other in their stability, physical properties, spectral data and methods of preparation. Three of these novel polymorphic forms are described in this application and are hereinafter referred to, respectively, as Form I, Form II, and Form IV.

Of the three novel polymorphs referred to above, Form I, exhibits the greatest stability. Form I is characterized by a minimum of five years crystalline stability.

This invention also relates to a pharmaceutical composition comprising an effective amount of a polymorph of Form I with any of the characteristics noted herein, and a pharmaceutically acceptable carrier or diluent thereof.

This invention also relates to a pharmaceutical composition comprising an effective amount of a polymorph of Form II with any of the characteristics noted herein, and a pharmaceutically acceptable carrier or diluent thereof This invention also relates to a pharmaceutical composition comprising an effective amount of a polymorph of Form IV with any of the above characteristics noted herein, and a pharmaceutically acceptable carrier or diluent thereof This invention further relates to the use of Form I for the treatment of a $PDE_4$ or TNF mediated disease in a mammal in need thereof, which method comprises administering to said mammal an effective amount of a polymorph of Form I with any of the characteristics noted herein.

This invention further relates to the use of Form II for the treatment of a $PDE_4$ or TNF mediated disease in a mammal in need thereof, which method comprises administering to said mammal an effective amount of a polymorph of Form II with any of the characteristics noted herein.

This invention further relates to the use of Form IV for the treatment of a $PDE_4$ or TNF mediated disease in a mammal in need thereof which method comprises administering to said mammal an effective amount of a polymorph of Form IV with any of the characteristics noted herein.

This invention results from a determination that certain batches of Cipamfylline showed differences in their IR mull spectra. All batches were prepared by the same route with ethanol as the final recrystallization solvent therefore it appeared possible that speed of crystallization may affect crystal form. In the light of this, recrystallized samples were prepared by crash cooling a portion of the hot liquid while the remainder was allowed to stand and crystallize unaided. In each case batch size was ca. 1 g or less. Samples were dried over silica gel under vacuum at room temperature. In this recrystallization program, three polymorphic forms have been positively identified, and are described herein as Forms I, II and IV.

Therefore, this invention also relates to a method of preparing a polymorph of Form I with any of the above characteristics comprising crystallizing Cipamfylline in an alcoholic solution of ethanol (s/f), propanol(s/f), butanol(s/f), isopropanol(s/f), or an organic solvent of ethyl acetate(s/f), toluene*, or as a solvent, water*. Under certain conditions, tetrahydrofuran (s/f), and acetone (s) may also be used.

In additional work with fast cooling, i.e. an ice water bath for use with smale scale samples, the time for the reaction temperature to drop from reflux to ambient takes approximately 1 minute with ethanol as a solvent.

In a prefered embodiment of this invention, 1-propanol is the solvent of choice to prepare Form I polymorphic forms.

This invention also relates to a method of preparing a polymorph of Form II with any of the above characteristics comprising crystallizing Cipamfylline in an alcoholic solution of methanol(s/f), or an organic solvent of tetrahydrofuran (s), or acetone (f). Under certain conditions, chloroform* or pyridine* may be used.

This invention also relates to a method of preparing a polymorph of Form IV with any of the above characteristics comprising crystallizing Cipamfylline in an organic solvent of 50:50 mixture of ethanol and isopropanol.

*Due to the particularly low solubility of Cipamfylline in solvent marked with an asterix.(*), such as toluene or water for Form I, the recrystallization procedure was modified, i.e. the hot solution was filtered to remove undissolved material and the filtrate was allowed to stand and crystallize out the compound.

The (s) term as used herein refers to slow, ambient recrystallization. It is noted that the term "slow" cooling (and "fast" cooling) are relative terms. In this particular meaning slow cooling may involve removal of the oil bath and air cooling. On the basis of scale alone (approximately 1 gm quantities for some experiments, versus a commerical batch size) cooling may actually be quite fast, such as in the 15 to 30 minute range. However, under controlled circumstances, slow cooling is generally defined as approximately one (1) hour from reflux to ambient temperature. Very slow cooling will be approximately from about four (4) hours from reflux to ambient. Under these conditions Form II may also be obtained from ethanol as described later in this document. However, similarly under the small batch sizes in some of the experiments used for Form I, the ethanol (slow cooling) route is not necessarily a reliable solvent/ temperature of choice for Form I. It is also noted that with regard to the use of acetone in fast cooling (i.e. use of an ice bath), Form I is formed. Limited analysis also indicates that use of acetone under the fast cooling route is not necessarily a reliable solvent/temperature of choice for Form II.

The (f) term as used herein refers to fast, crash cool recrystallization, such as by placing the flask in a ice water bath, or similar techniques for larger scale processing.

These three novel crystalline polymorphs of Cipamfylline, also referred to as BRL 61063, all melt at about 305° C. to about 313° C.

The crystalline polymorph, Form I, exhibits a characteristic X-ray powder diffraction pattern with characteristic peaks expressed d spacing (A) in decreasing intensity, at 12.302, 7.702, 8.532. 4.289, and 2.854 as depicted in FIG. 1. A discussion of the theory of X-ray powder defraction patterns can be found in Stout & Jensen, X-Ray Structure Determination; A Practical Guide, Mac Millian Co., New York, N.Y. (1968).

Figure 2:
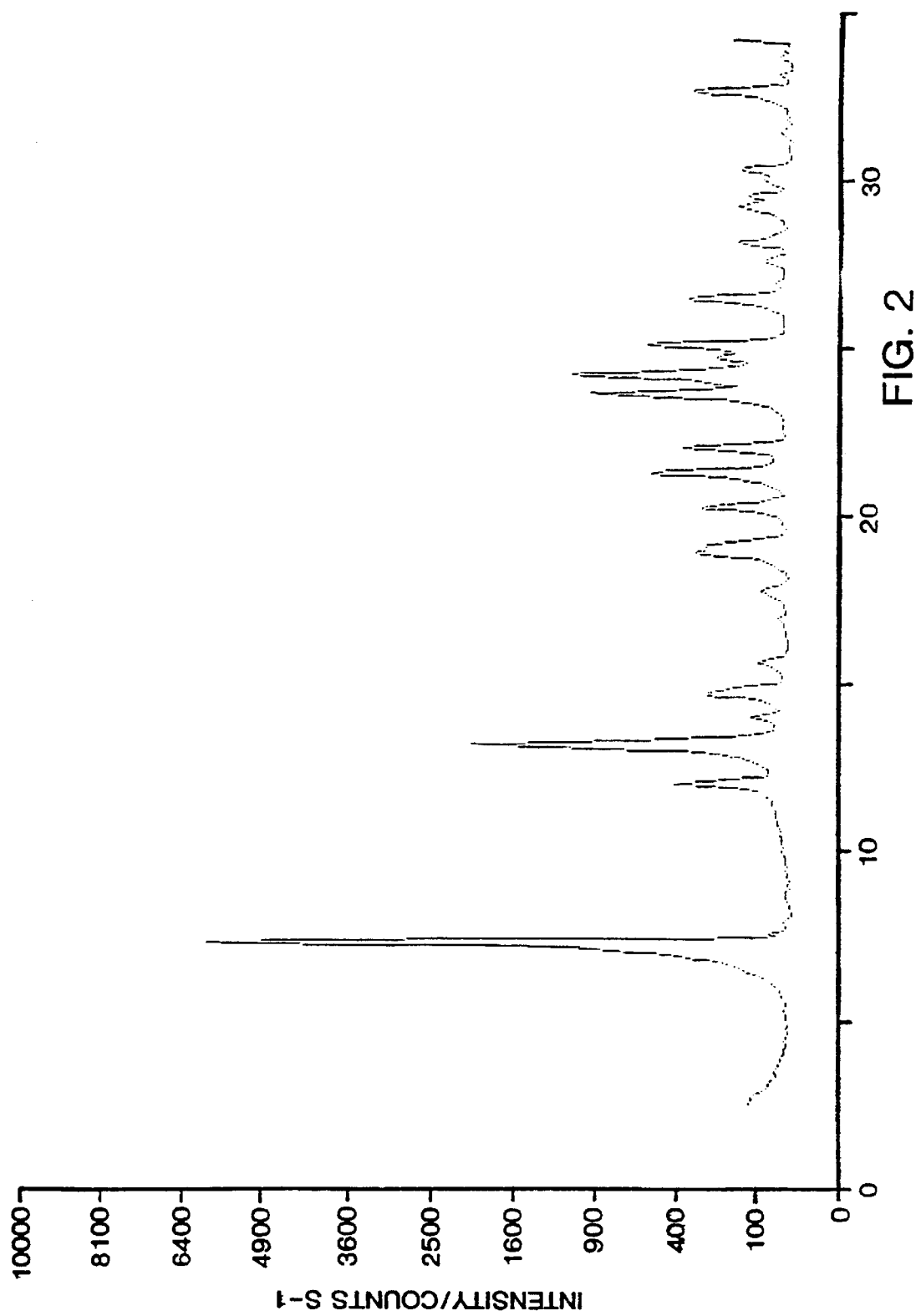
FIG. 2 is a characteristic X-ray powder diffraction pattern for Form II. (Vertical axis: Intensity (CPS); Horizontal axis: Diffraction Angle, in Two Theta (degrees)).

The crystalline polymorph, Form II, exhibits a characteristic X-ray powder diffraction pattern with characteristic peaks expressed d spacing (A) in decreasing intensity,. at 12.001, 6.702, 3.687, 3.773, and 7.345 as depicted in FIG. 2.

This invention also relates to the crystalline polymorph Forms I, II, and IV, of Cipamfylline that are further characterized by the crystal parameters obtained from single crystal X-ray crystallographic analysis as set forth in Tables 1, 2 and 3 below. The 3-D X-ray data was collected at ambient temperatures.

TABLE I

Crystal Parameters of Form I

| | |
|---|---|
| Crystal Shape (mm): | Flat needles |
| Crystal Dimensions: | 1.0 × 0.12 × 0.08 mm |
| Crystal Color: | Colorless |
| Space Group: | P1 triclinic #2 |
| Temperature: | 295K |
| Cell Constants: | a = 10.829(2)Å |
| | b = 12.636(2)Å |
| | c = 5. 105(3)Å |
| | alpha (α) = 99.48(4) |
| | beta (β) 91.53(4) |
| | gamma (γ) = 83.84(3) |
| Volume: | 685.0(8)Å$^3$ |
| Molecules/unit cell (Z) | 4 |
| ρ (calc), Density | 1.354 g/cm$^{-3}$ |
| | 7.362 cm$^{-1}$ |
| F(000) | 292 |

TABLE II

Crystal Parameters of Form II

| | |
|---|---|
| Crystal Shape (mm): | Rectangular blocks |
| Crystal Colour: | Colorless |
| Crystal Dimensions: | 0.80 × 0.50 × 0.15 mm |
| Space Group | P2$_{1/c}$ monoclinic #14 |
| Cell Constants | a = 12.227(4)Å |
| | b = 7.448(2)Å |
| | c = 14.946(8)Å |
| | alpha (α) = 90(4) |
| | beta (β) 97.95(4) |
| | gamma (γ) = 90(4) |
| Volume | 1348.1(9)Å$^3$ |
| Molecules/unit cell (Z) | 4 |
| ρ (calc) Density | 1.356 g/cm$^{-3}$ |
| μ | 0.896 cm$^{-1}$ |
| F(000) | 584 |

TABLE III

Crystal Parameters of Form IV

| | |
|---|---|
| Crystal Shape (mm) | Flat needles |
| Crystal Color | Colorless |
| Crystal Dimensions | 0.60 × 0.10 × 0.05 mm |
| Space Group | P1 triclinic #2 |
| Temperature | 295K |
| Cell Constants | a = 10.210(3) Å |
| | b = 13.753(2) Å |
| | c = 4.942(31) Å |
| | alpha (α) = 97.94(2) |
| | beta (β) = 97.95(4) |
| | gamma (γ) = 83.33(2) |
| Volume | 677.1(5) Å$^3$ |
| Molecules/unit cell (Z) | 2 |
| ρ (calc) Density | 1.350 g/cm$^{-3}$ |
| μ | 7.448 cm$^{-1}$ |
| F(000) | 292 |

The unit cell dimension is defined by three parameters; length of the sides of the cell, relative angles of sides to each other and the volume of the cell. The lengths of the sides of the unit cell are defined by a, b and c. The relative angles of the cell sides are defined by alpha, beta, and gamma. The volume of the cell is defined as V. A more detailed account of unit cells can be found in Chapter 3 of Stout & Jensen, X-Ray Structure Determination; A Practical Guide, Mac Millian Co., New York, N.Y. (1968).

The crystalline state of a compound can be unambiguously described by several crystallographic parameters: unit cell dimensions, space group, and atomic position of all atoms in the compound relative to the origin of its unit cell. These parameters are experimentally determined by single crystal X-ray analysis. It is possible for a compound to form more than one type of crystal. These different crystalline forms are called polymorphs. It has now been discovered that there are three polymorphic forms of Cipamfylline. This discovery was confirmed by three separate single crystal X-ray analysis. A comparison of the unit cell dimensions and space groups of these three crystalline states are shown in Tables 1 to 3 above. Plotting the atomic positions, for the three polymorphs, of the atoms derived from the single crystal X-ray analysis confirms that the crystals contain Cipamfylline and no other molecules of crystallization or impurity.

Figure 10:
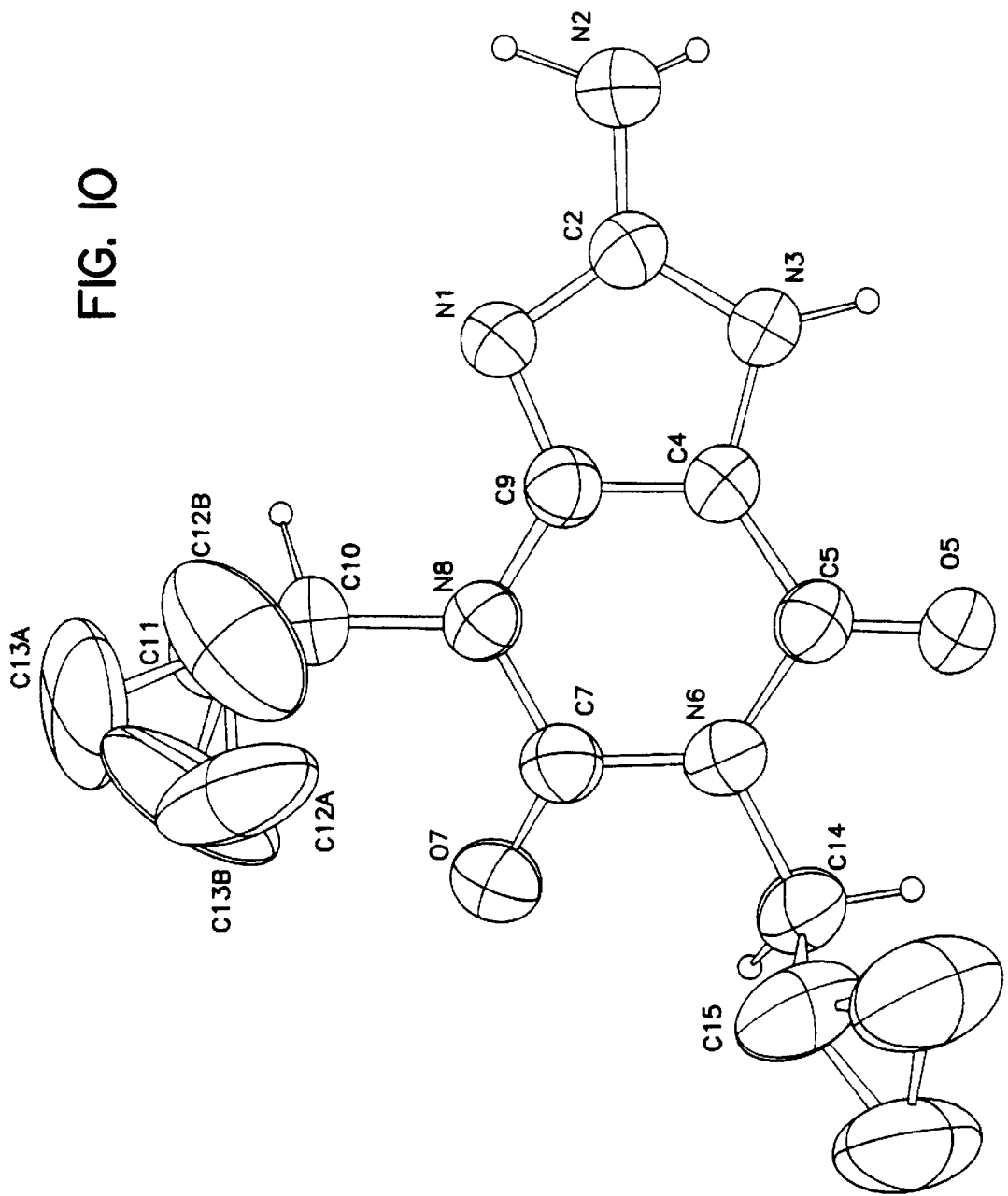
FIG. 10 depicts the Form I molecule in three dimensions and with a labeling scheme.
Figure 16:
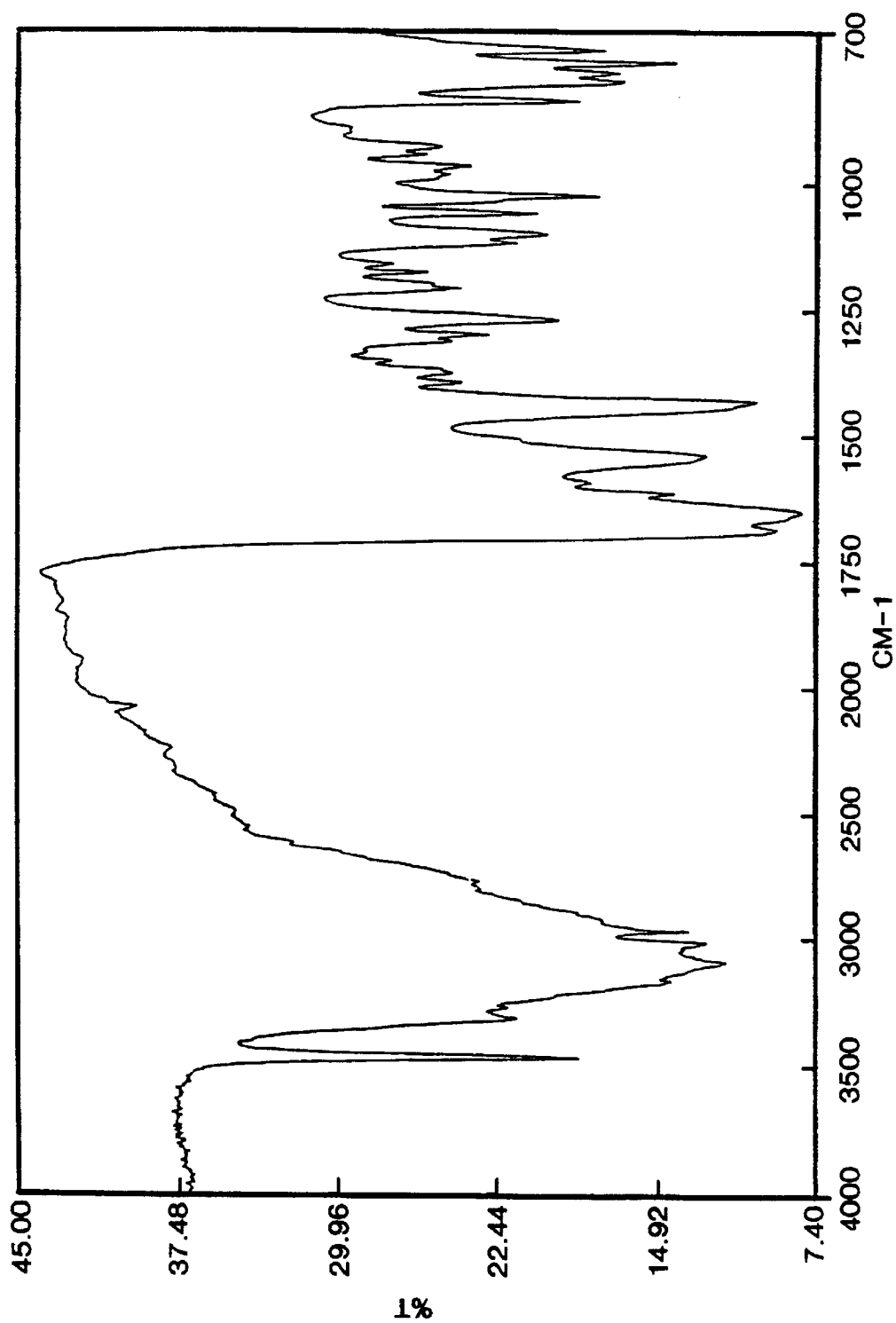
FIG. 16 is a characteristic infrared absorption spectrum of a single crystal of Form I.
Figure 17:
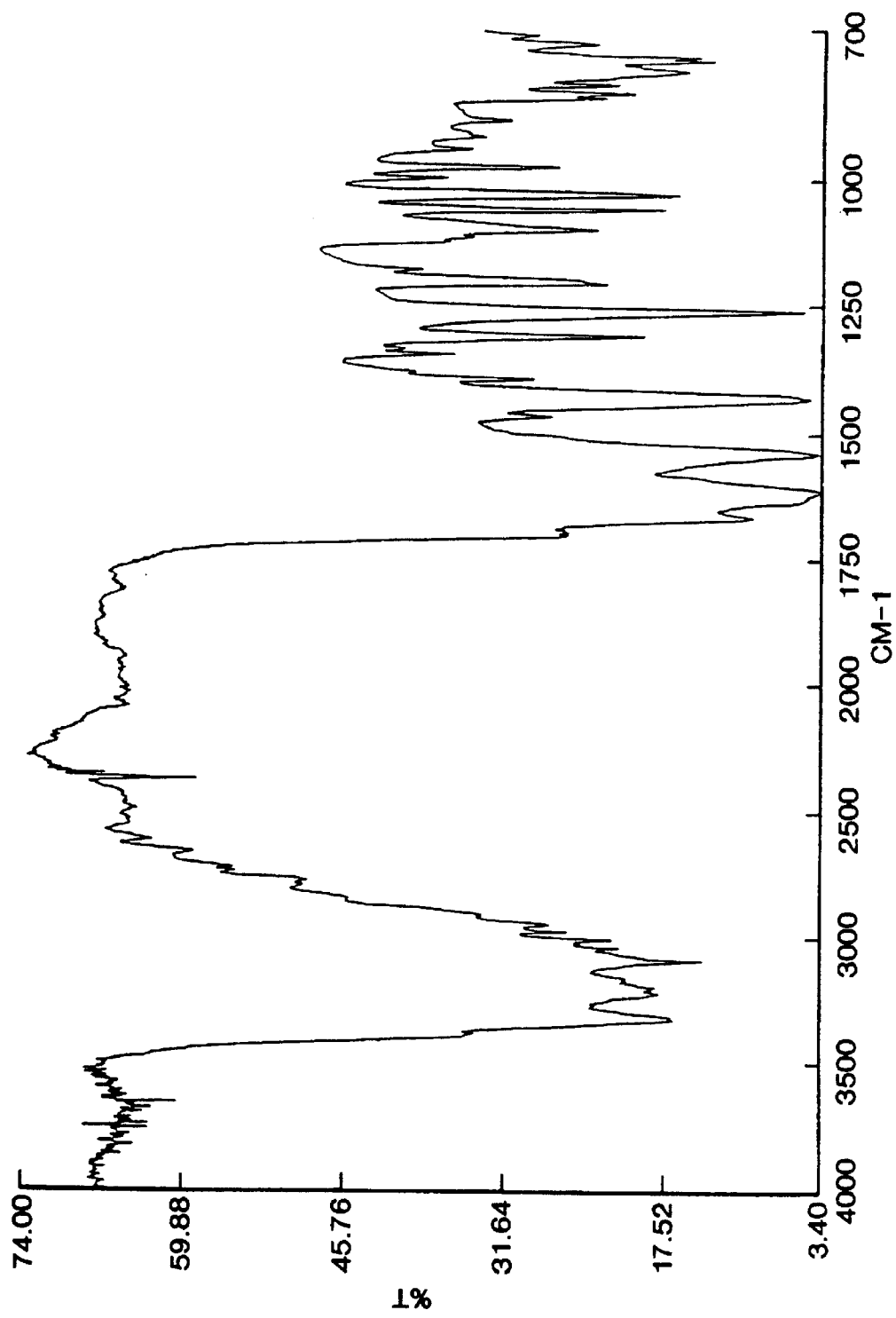
FIG. 17 is a characteristic infrared absorption spectrum of a single crystal of Form II.
Figure 18:
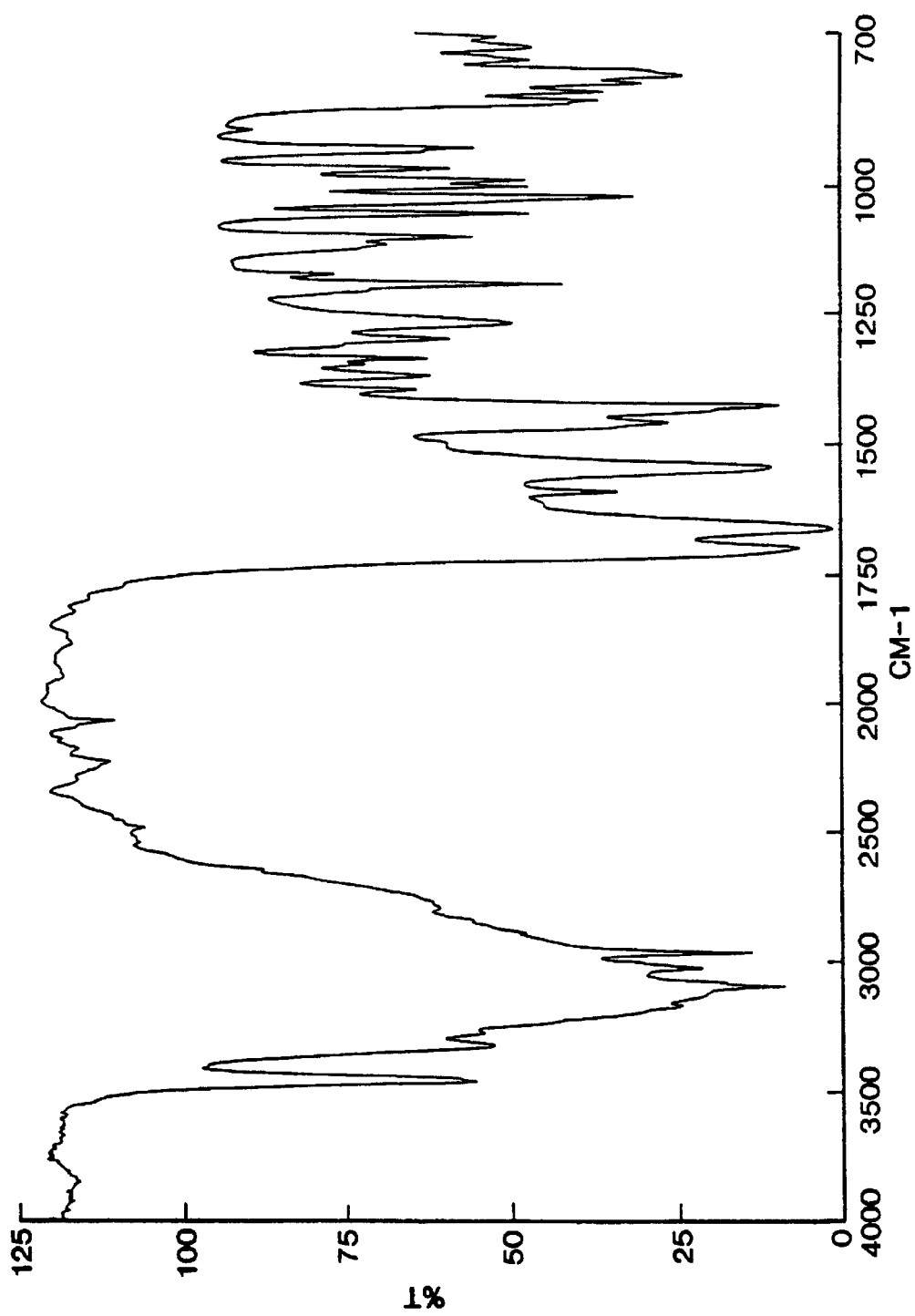
FIG. 18 is a characteristic infrared absorption spectrum of a single crystal of Form IV.
Figure 19:
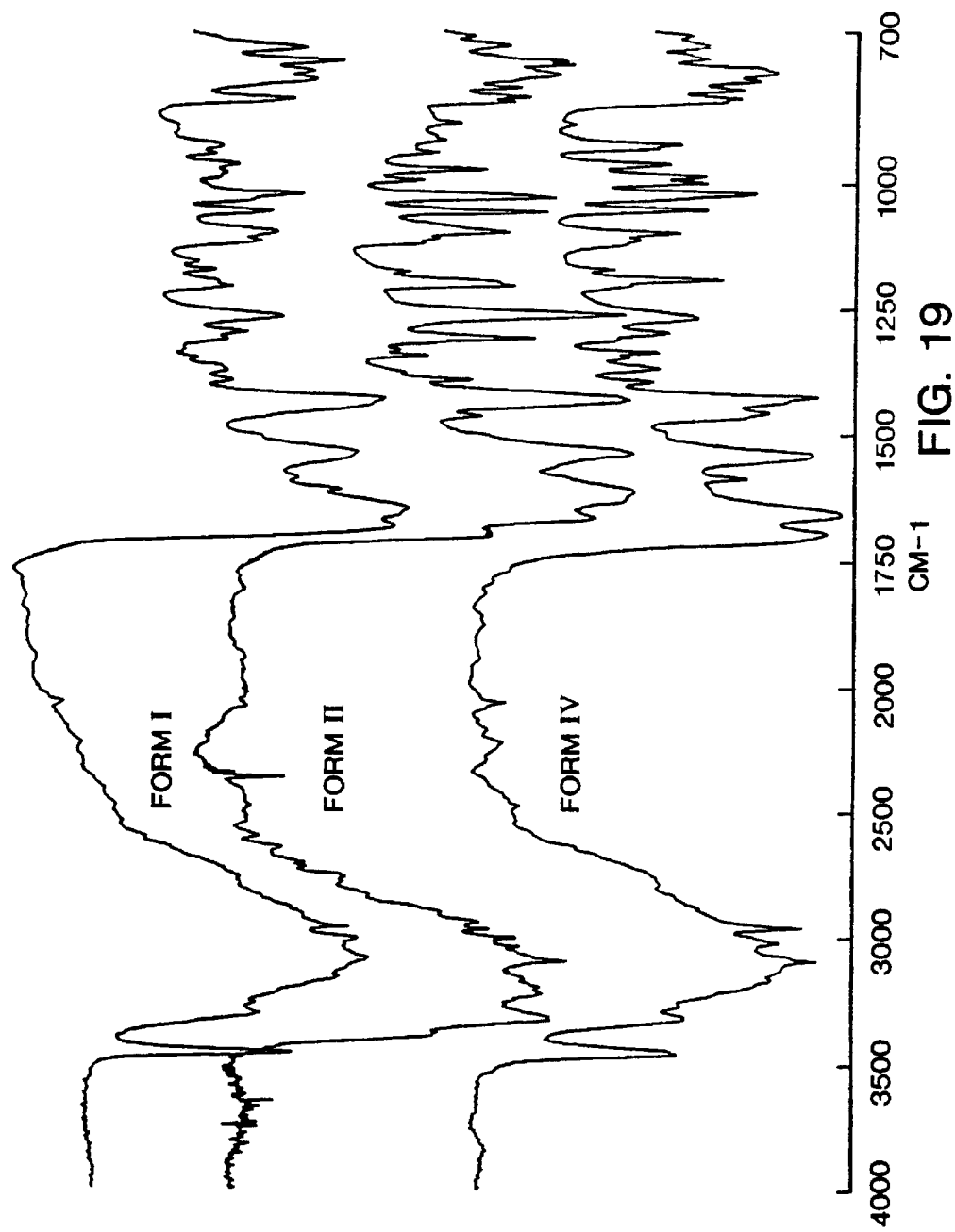
FIG. 19 is a comparison of characteristic infrared absorption spectra of the single crystals of Forms I, II and IV.
Figure 20:
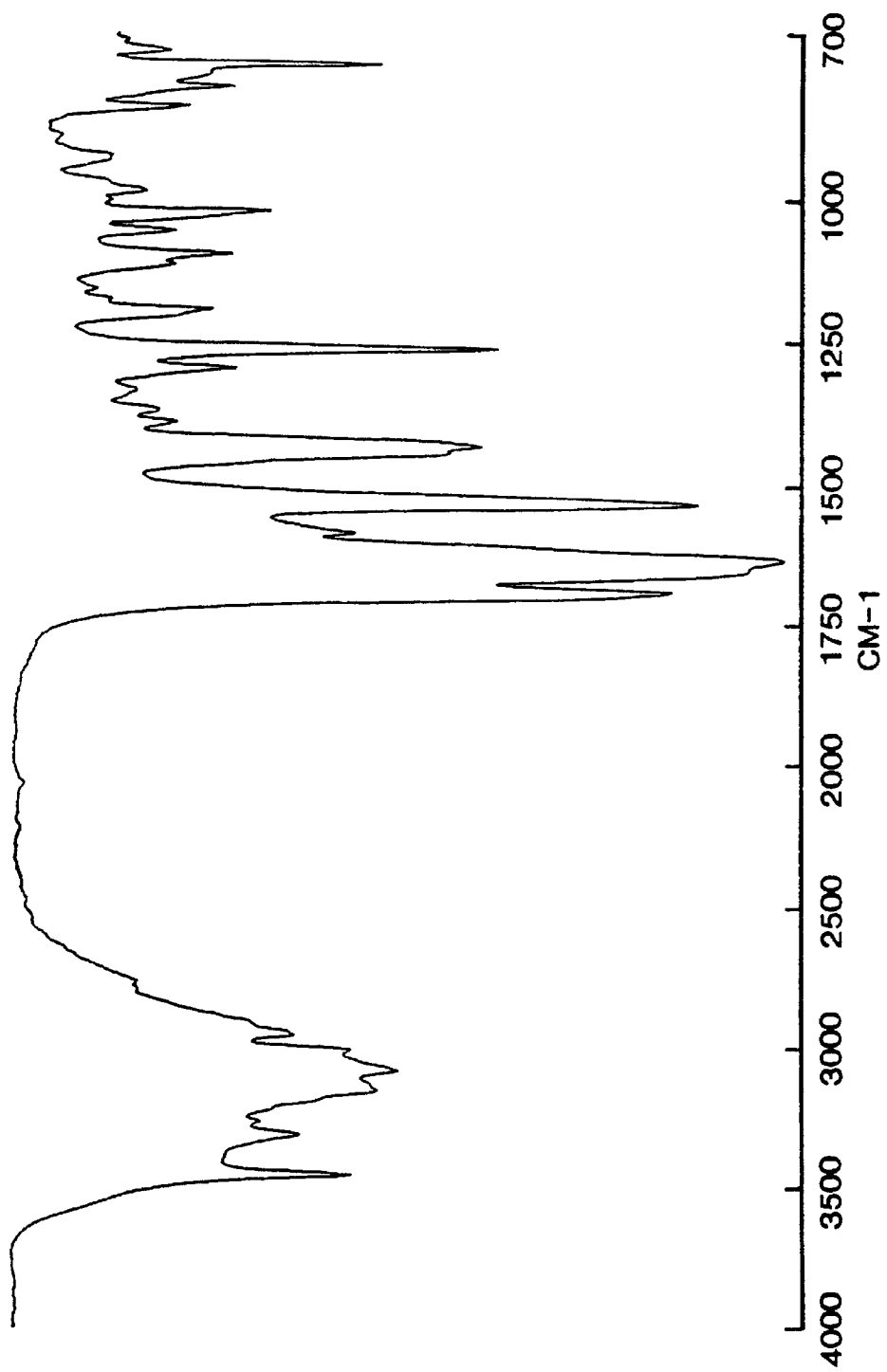
FIG. 20 is a characteristic infrared absorption spectrum in potassium bromide of Form I. (Vertical axis: Transmission (%); Lower horizontal axis: (Wavenumber (cm<-1>)).
Figure 21:
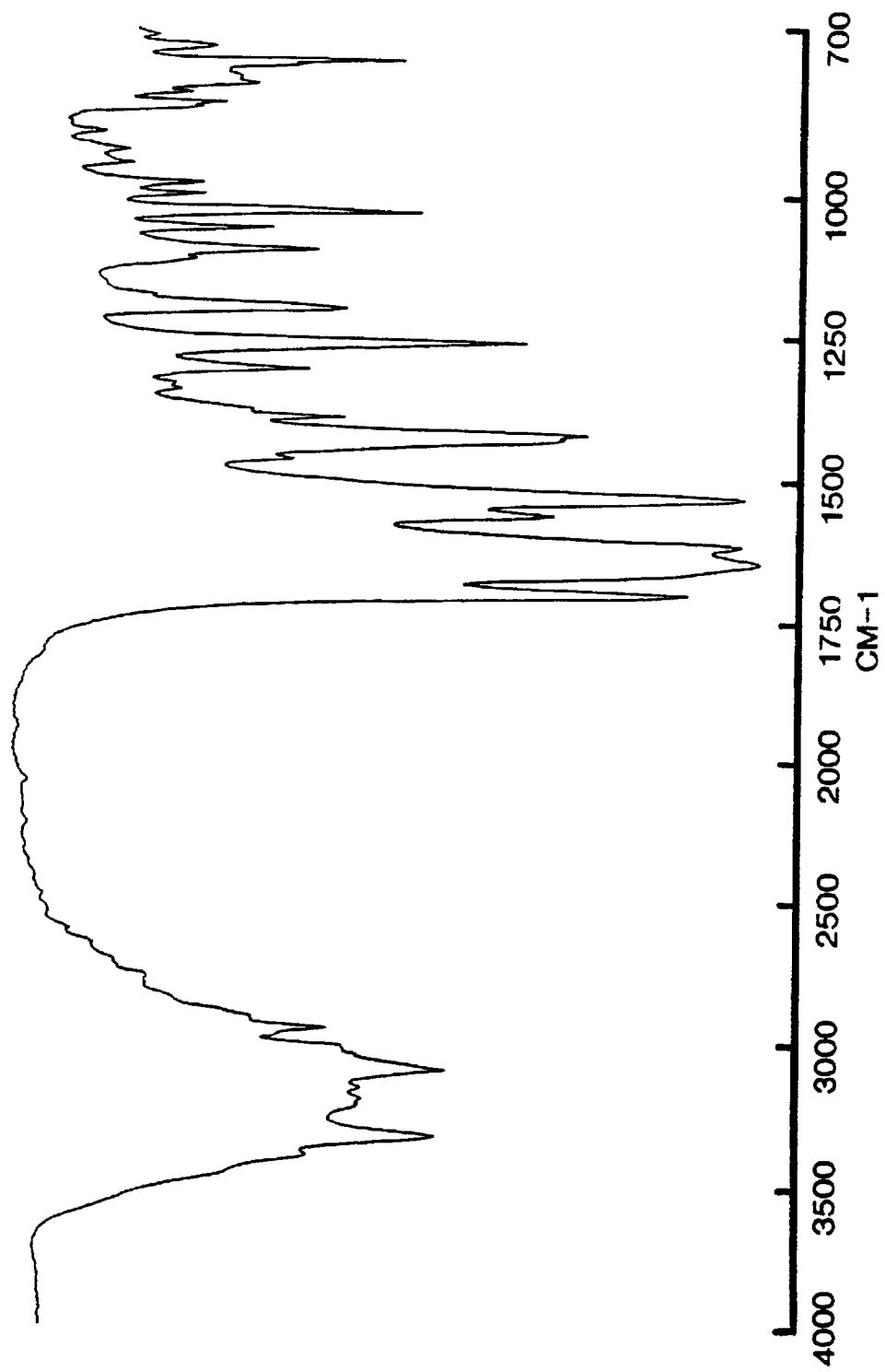
FIG. 21 is a characteristic infrared absorption spectrum in potassium bromide of Form II. (Vertical axis: Transmission (%); Lower horizontal axis: (Wavenumber (cm<-1>)).
Figure 22:
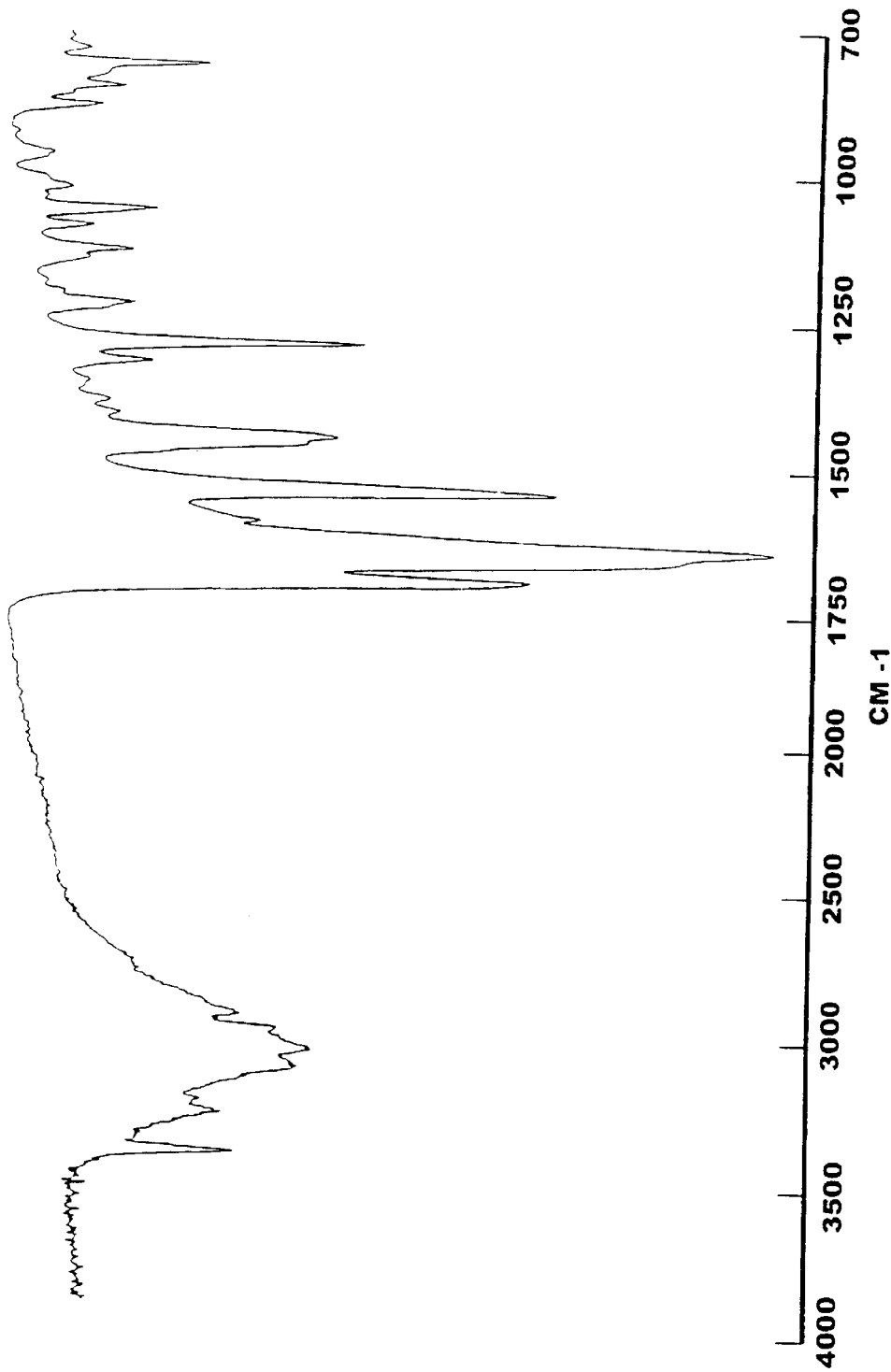
FIG. 22 is a characteristic infrared absorption spectrum of a crushed crystal of Form I.
Figure 23:
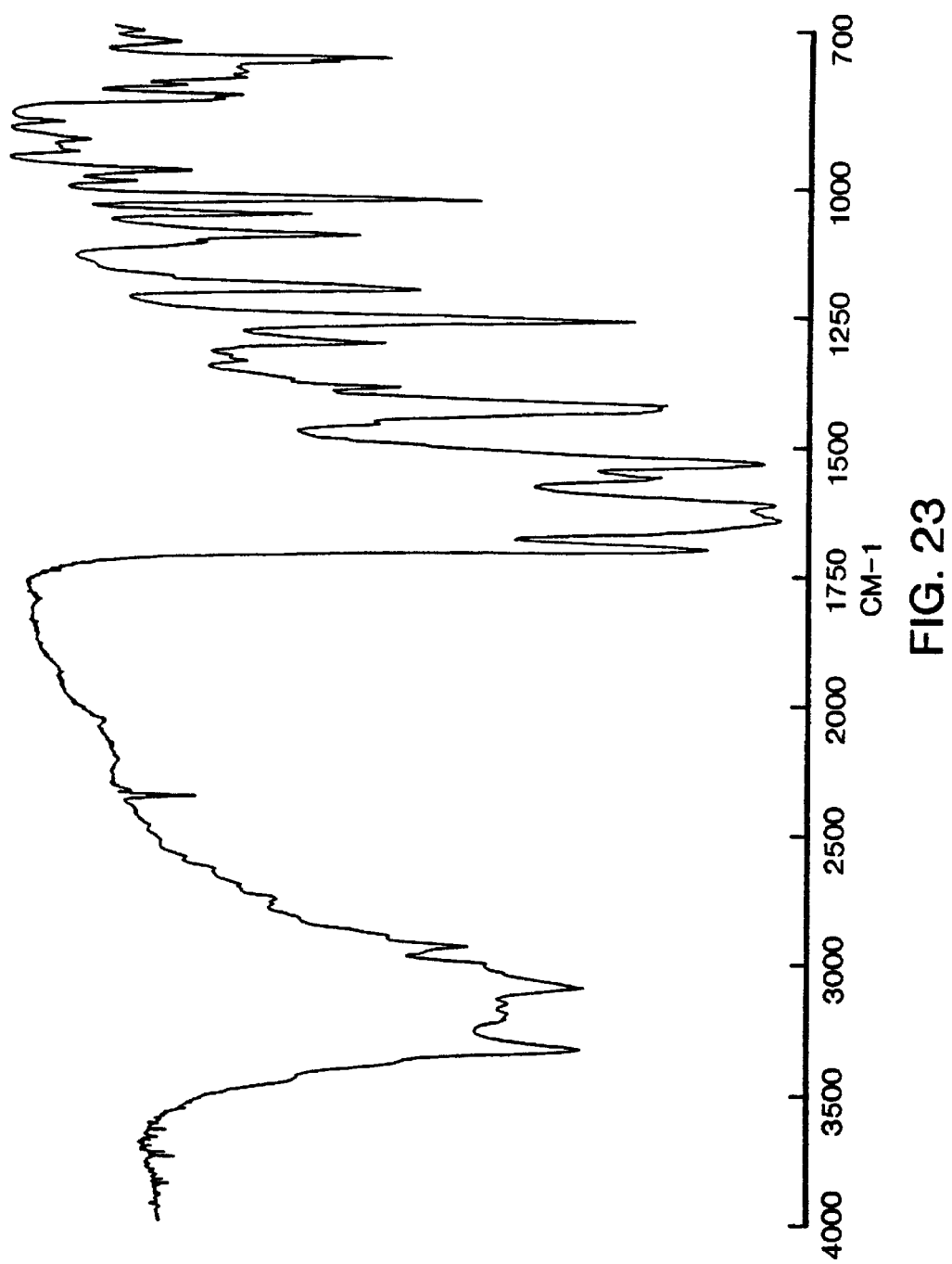
FIG. 23 is a characteristic infrared absorption spectrum of a crushed crystal of Form II.
Figure 24:
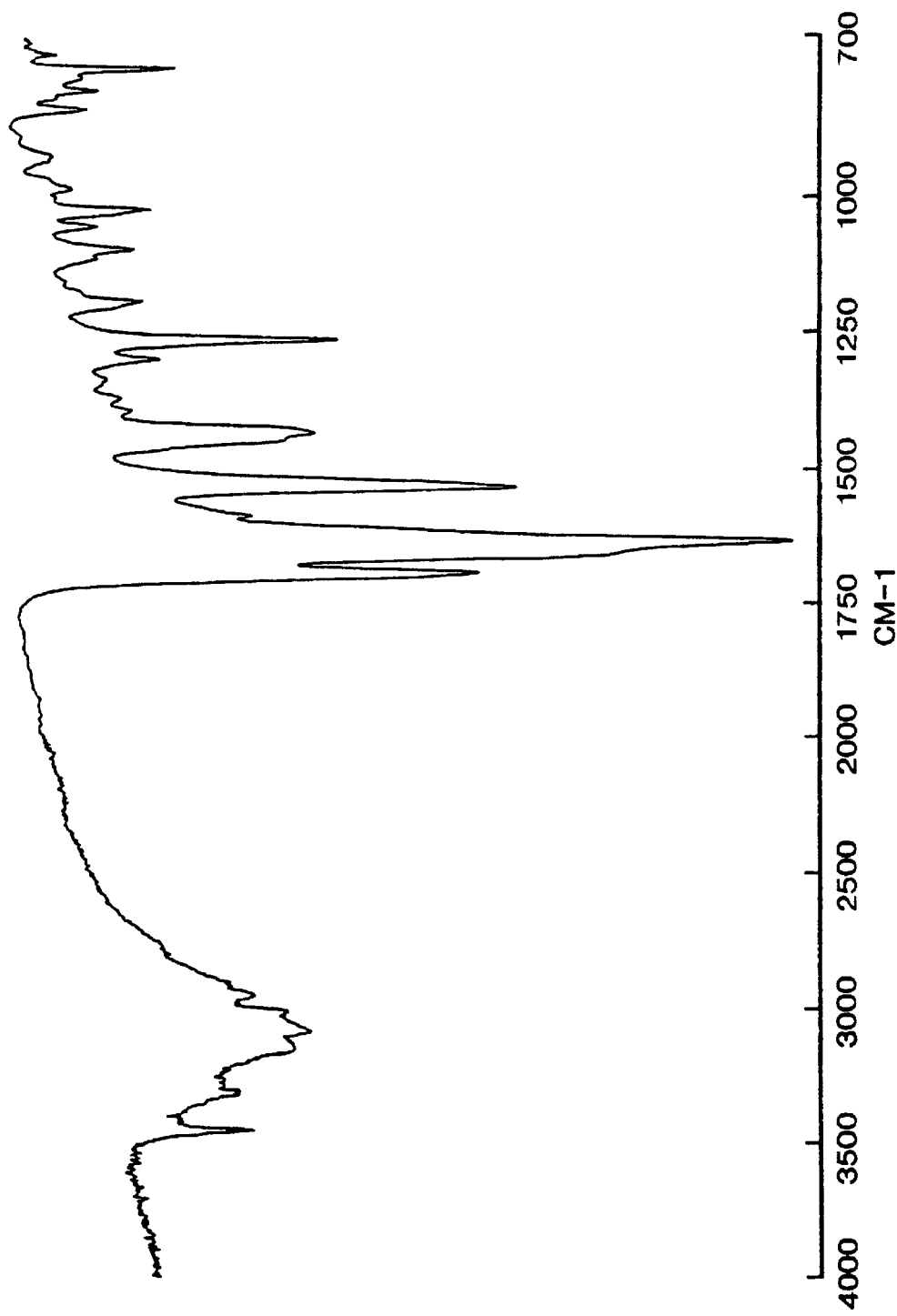
FIG. 24 is a characteristic infrared absorption spectrum of a crushed crystal of Form IV.
Figure 25:
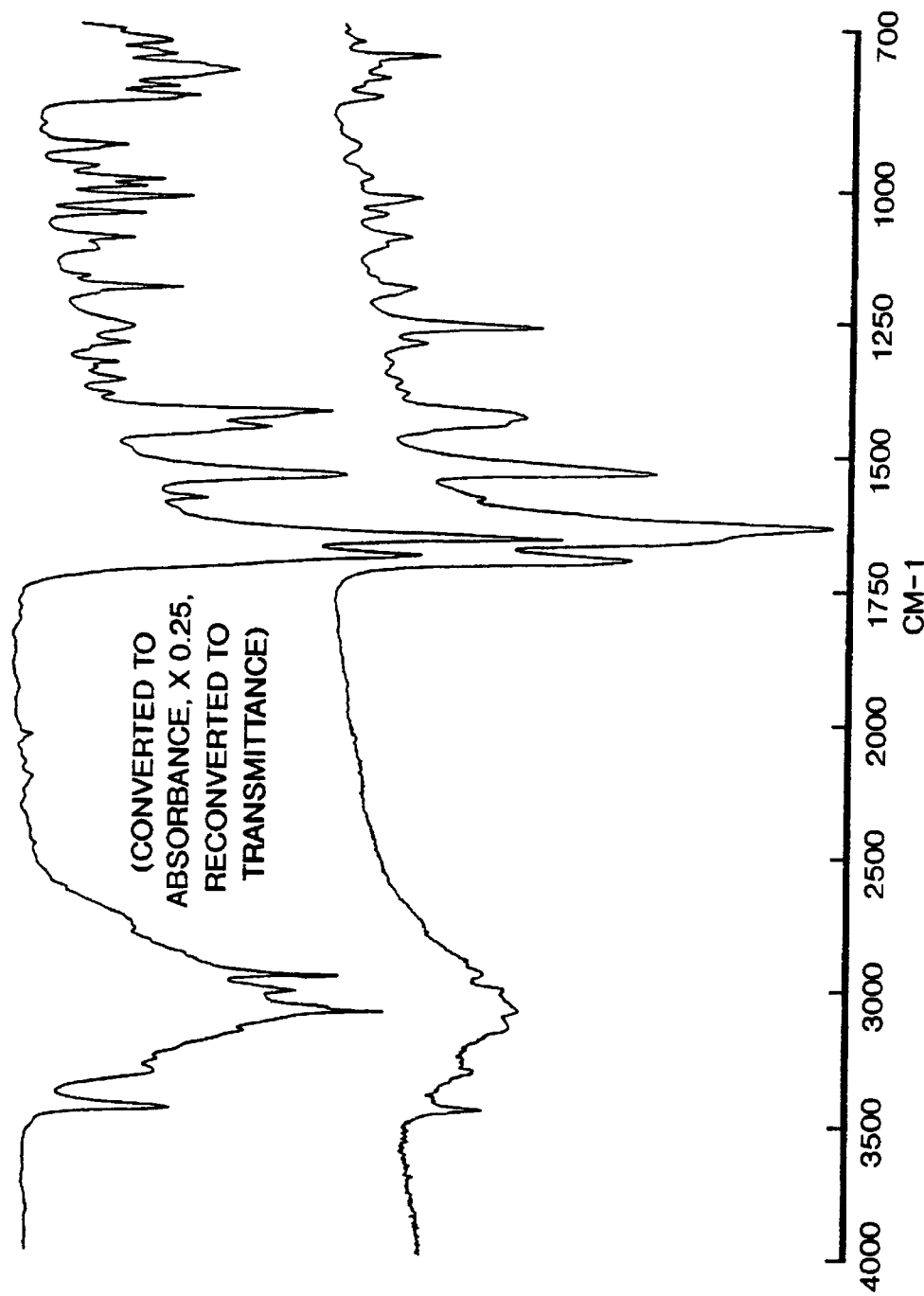
FIG. 25 is a comparison of the infrared absorption spectra of a single and crushed crystal of Form IV.

FIG. 10 depicts the molecule in three dimensions and with a labeling scheme. FIG. 11 provides for a stereo drawing. Overall, the molecular conformation observed in Form 1 is identical to that of Form IV, with the exception of a clear disorder in one of the cyclopropyl groups (atoms C12 and C13), which was modeled with two positions of equal occupancy for each of these atoms. The high degree of thermal motion in the other cyclopropyl group (atoms C16 and C17) suggests that it may be experiencing conformational flexing.

The unit cell of Form I crystals is of the same form as that of Form III, with similar cell dimensions, a volume of 8 Å$^3$ larger, and correspondingly, a density reduced by 0.15 g cm$^{-3}$. All of these effects are in keeping with the presence of disorder in the channel which the cyclopropyl groups occupy.

Hydrogen bonding in this crystal structure is all intermolecular in nature and is similar, in terms of specific interactions to that seen in Form IV. As in the Form IV structure, the positions of the amino hydrogens are indicated from difference Fourier electron density maps. The position of H2N2 is not consistent with the participation of that hydrogen in a hydrogen bonding interaction. A distance of 3.399(3)Å between atoms N2 and O5 in Form I, however, suggest the possibility of a weak interaction analogous to that observed in Form II structure, although the distance observed in this form is longer by 0.4 Angstroms. When a position for H(2)N(2) was calculated which would satisfy this hydrogen bonding interaction, and attempts were made to refine it, the thermal value became unreasonable large, suggesting that the data do not support this alternative position. Thus the refinement was completed with H2N2 in its original location as indicated by difference Fourier synthesis. The associated metrical details of the other two hydrogen bond are:

| Summary of hydrogen-bonding of Form I | | |
|---|---|---|
| H-bonding atoms | Atom-atom distance | Angle |
| N(2)—N(1) | 3.067(3)Å | 173(3)° |
| H(1)N(2)—N(1) | 2.16(3)Å | |
| N(3)—O(5) | 2.793(3)Å | 165(4)° |
| HN(3)—O(5) | 2.02(3)Å | |

Figure 26:
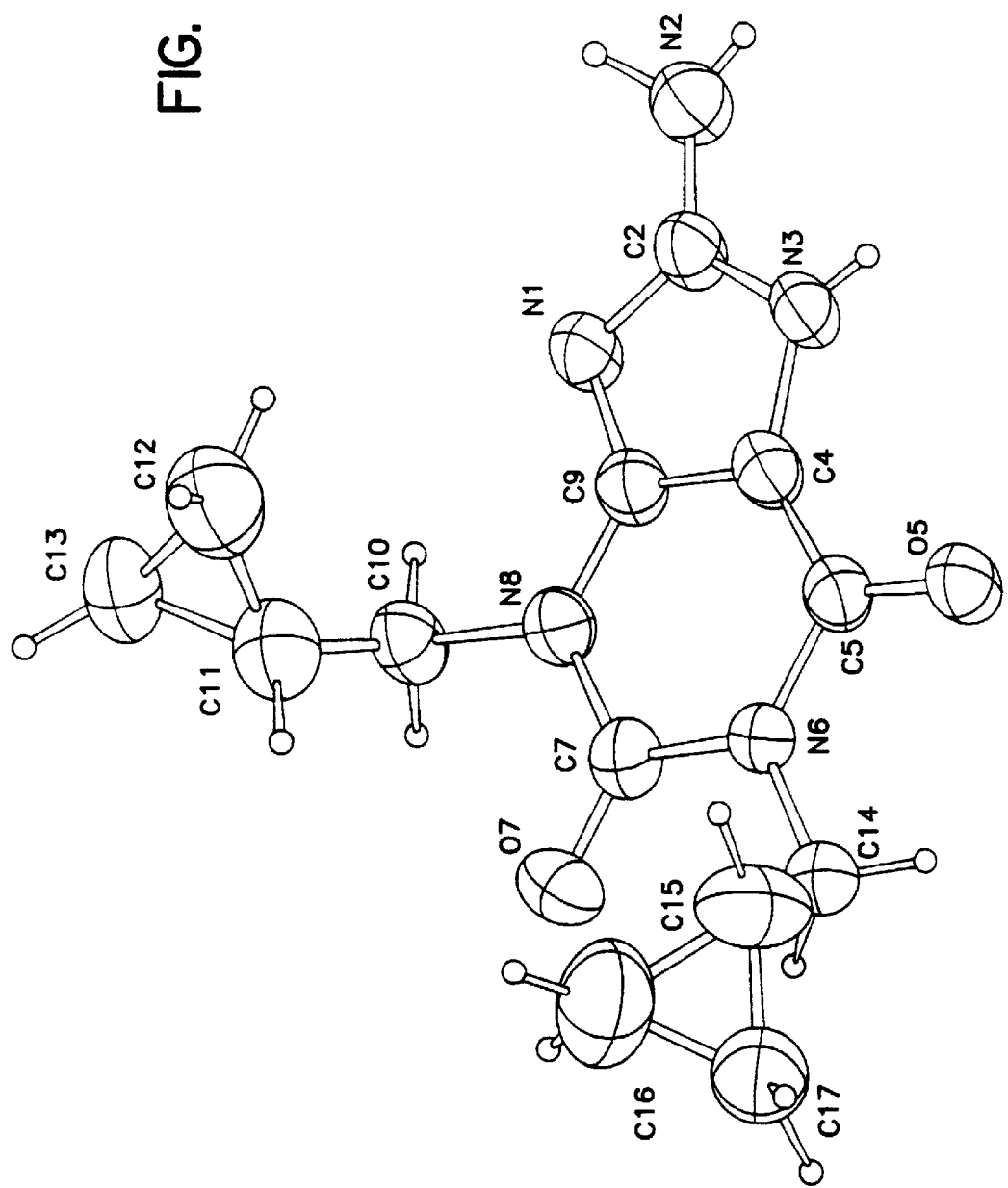
FIG. 26 depicts the Form IV molecule in three dimensions and with a labeling scheme.
Figure 27:
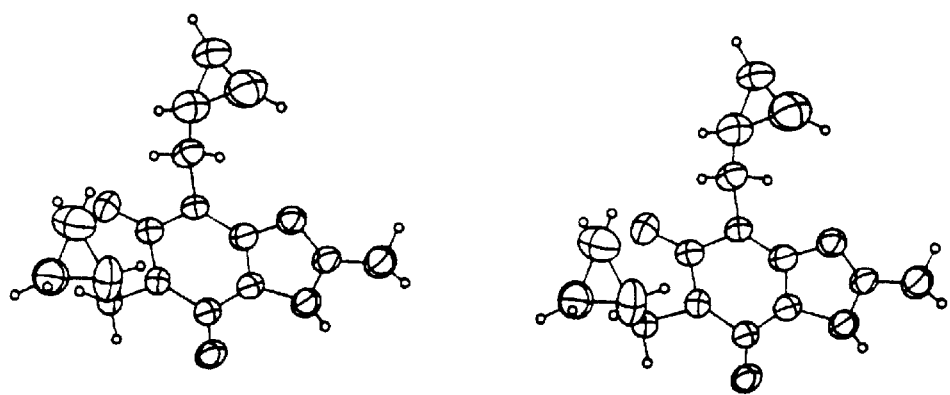
FIG. 27 provides for a stereo drawing of the Form IV molecule.

With regard to Form IV, FIG. 26 depicts the molecule in three dimensions and with a labeling scheme. FIG. 27 provides for a stereo drawing of Form IV. For the data described in this section, crystals of Form IV were grown from a 50/50 mixture of ethanol and isopropanol by slow evaporation. Further, crystals of Form II were also grown from this solvent mixture with Form II crystals appearing to nucleate first, with needles of Form IV coming after the solution has evaporated for several days. Overall the molecular conformation observed in Form IV is very similar to that of Form II. Principal differences are concentrated in the rotational orientation of the cyclopropyl groups which display a nearly enantiomorphous relationship to their counterparts in the Form II structure, as summarized in the torsion angle tabulation Table 4, and shown in FIG. 3 herein.

Hydrogen bonding in the crystal structure for Form IV is all intermolecular in nature and is similar, in terms of specific interactions to that seen in Form II. A major difference involves one of the two hydrogens on N2. There is a clear indication of the position for H1N2 in difference difference Fourier electron density maps. The position is not consistent with the participation of that hydrogen in a hydrogen bonding interaction. A distance of 3.273(3)Å between atoms N2 and O5 in Form IV, however, suggest the possibility of a hydrogen bonding interaction analogous to that observed in Form II structure, although the distance observed in this form is longer by 0.2 Å. When a position for H1N2 was calculated which would satisfy this hydrogen bonding interaction, and attempts were made to refine it, the thermal value became unreasonable large, suggesting that the data do not support this alternative position. Thus the refinement was completed with H1N2 in its original location as indicated by difference Fourier synthesis. The associated metrical details of the other two hydrogen bond are:

| Summary of hydrogen-bonding of Form IV | | |
|---|---|---|
| H-bonding atoms | Atom-atom distance | Angle |
| N(2)—N(1) | 3.042(2)Å | 173(2)° |
| H(1)N(2)—N(1) | 2.10(2)Å | |
| N(3)—O(5) | 2.731(2)Å | 160(2)° |
| HN(3)—O(5) | 1.91(2)Å | |

Figure 32:
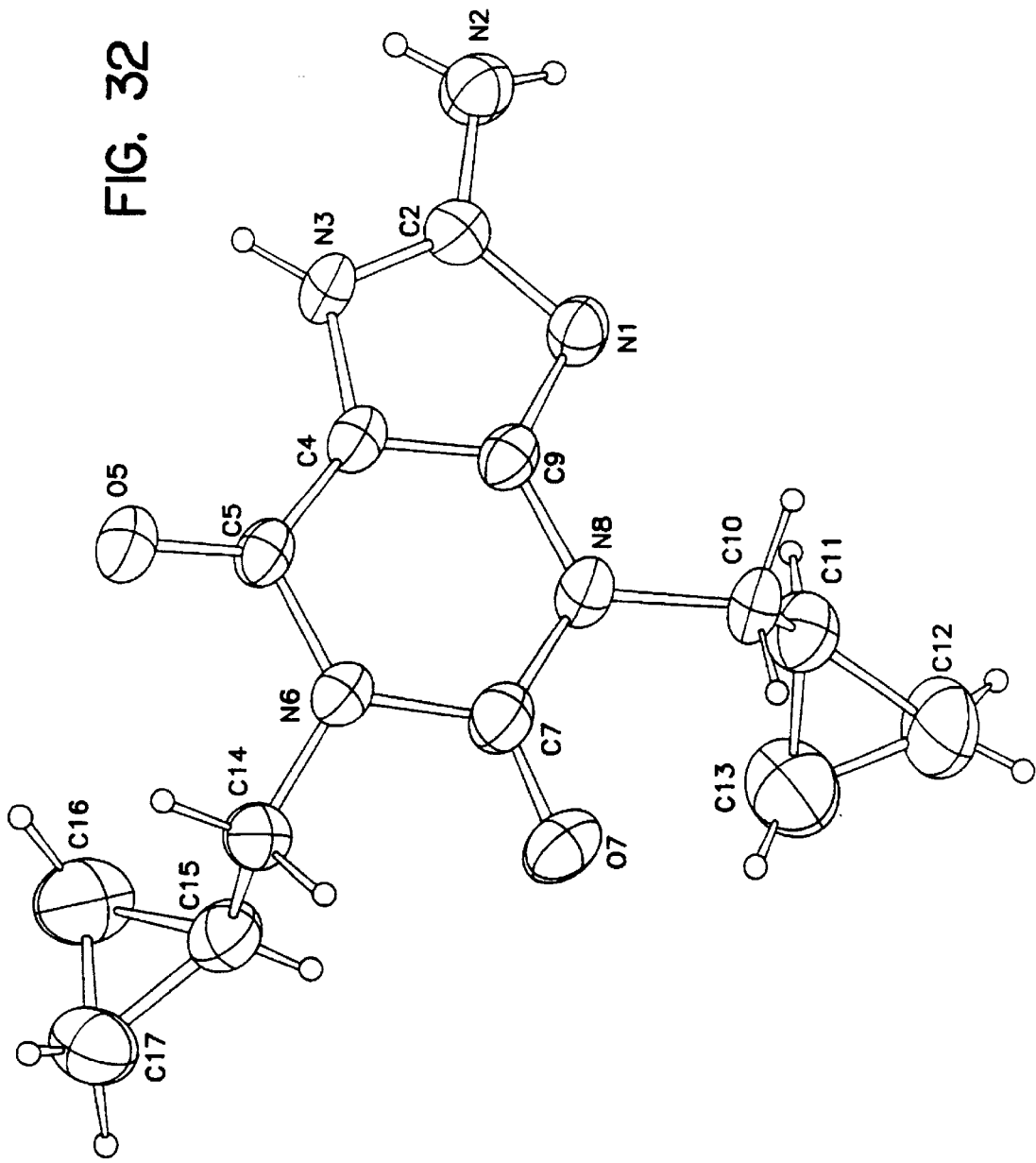
FIG. 32 depicts the Form II molecule in three dimensions and with a labeling scheme.

With regard to Form II, FIG. 32 depicts the Form II molecule in three dimensions and with a labeling scheme. The hydrogen bonding for the crystal structure of polymorph Form II, is all intermolecular in nature. The associated meterical details are:

| Summary of the hydrogen bonding of Form II | | |
|---|---|---|
| H-bonding atoms | Atom-atom distance | Angle |
| N2—O5 | 3.049(3)Å | Angle 151(2)° |
| H1N2—O5 | 2.26(3)Å | |
| N2—N1 | 3.071(3)Å | Angle 137(3)° |
| H2N2—N1 | 2.41(3)Å | |
| N3—O5 | 2.741(3)Å | Angle 168(2)° |
| HN3—O5 | 1.90(3)Å | |

This structural information clearly shows that Forms I, II, and IV of Cipamfylline are all crystallographically different. The hydrogen bonding in all the forms is intermolecular in nature, and all three possess hydrogen bonding between HN(2)—N(1) and HN(3)—O(5).

Experimental Details

Form I

Flat needles were grown by slow evaporation from a mixture of ethyl acetate and butanol. Lattice parameters were determined from the setting angles of 25 reflections well distributed in reciprocal space measured on an Enraf Nonius CAD-4 diffractometer, and are further described in Table 5 below. A full sphere of intensity data also were collected on the diffractometer using graphite monochromated copper radiation from a rotating anode source and an ω-2θ variable speed scan technique. Intensities of three monitor reflections measured at the beginning, end and every two hours of exposure time changed by at most +/−0.1%. Three orientation controls also were monitored to assess any crystal movement during the experiment. Data were corrected for Lorentz and polarization effects, and using the DIFABS algorithm, for the effects of absorption. Redundant observations were averaged to obtain the final data set.

The structure was solved by direct methods using the SHELXS program series. Atomic positions were initially refined with isotropic temperature factors and subsequently with anisotropic displacement parameters. The function minimized was $\Sigma w(|Fo|-|Fc|)^2$. Weights, w, were eventually assigned to the data as w=1/σ2 (fo)={$\sigma^2$(Ic)+(0.04I)$^2$}. Positions for the hydrogen atoms attached to nitrogens were discovered in subsequent difference Fourier maps. Positions for hydrogen atoms attached to carbons were calculated based on geometrical considerations and held fixed in the final refinement stages along with isotropic temperature factors assigned 1.3(Beq) of the attached atom. Hydrogen atoms on the cyclopropyl groups were omitted from the refinement. All other hydrogen positions were refined along with isotropic temperature factors. The full matrix least-squares refinement converged (max $\Delta/\sigma=0.05$) top values of the conventional crystallographic residuals R=0.056, wR=0.092. A final difference Fourier map was featureless with maximum density of +/−0.285 e$\text{Å}^{-3}$. Values of the neutral atom scattering factors were taken from the International Tables for X-ray Crystallography.

TABLE 5

Intensity Measurement Data for Form I

| | |
|---|---|
| Diffractometer: | Enraf Nonius CAD4 |
| Radiation: | CuKα λ = 1.5406Å |
| Monochromator: | Graphite Single Crystal |
| Scan Technique | ω-2θ scan |
| Scan Speed: | Variable 1.50 to 6.7 deg min$^{-1}$ in ω |
| Background Measurements | Moving crystal-moving counter at each end of the scan range; scan time/background time = 2.0 |
| Range of Data: | 20 ≦ 2θ ≦ 60° |
| | −12 ≦ h ≦ 12 |
| | −14 ≦ k ≦ 14 |
| | −5 ≦ 1 ≦ 5 |
| Standard Reflections: | Three standards measured every three hours of x-ray exposure time |
| Total No. Reflections; | 2320 |
| | 2032 unique |
| Rint: | 1.2% |
| No. of Observed Data | 1749 I> 3 σ(I) |
| No. of Variables: | 199 |
| p: | 0.04 |
| R: | 0.056% |
| Rw: | 0.092% |
| Goodness of Fit: | 3.311 |
| Absorption Correction: | 0.868 min 1.254 max 0.991 ave |

The complete single crystal X-ray experimental data used to produce the structure displayed in FIG. 10 for Form I is included in FIGS. 12 to 15. The parameters presented in the tables are measured in units commonly used by those skilled in the art. A more detailed discussion of the units of measure can be found in International Tables for X-ray Crystallography, Vol. IV, pp. 55, 99, 149 Birmingham: Kynoch Press, 1974, and G. M. Sheldrick, SHELXTL. User Manual, Nicolet Instrument Co., 1981.

Form II

Rectangular plates were grown by slow evaporation from a solution prepared in methanol/2-butanone. Lattice parameters were determined from the setting angles of 25 reflections well distributed in reciprocal space measured on an Enraf Nonius CAD-4 diffractometer, and further described in Table 6. Intensity data also were collected on the diffractometer using graphite monochromated molybdenum radiation and an ω-2θ variable speed scan technique. A correction was applied to the data for a 4.8% decrease in the intensities of three monitor reflections measured at the beginning, end and every two hours of exposure time. Three orientation controls also were monitored to assess any crystal movement during the experiment. Data were corrected for Lorentz and polarization effects, and using the DIFABS algorithm, for the effects of absorption. Symmetry equivalents and zonal reflections were averaged to obtain the final data set.

The structure was solved by direct methods using the MULTAN80 program series. Atomic positions were initially refined with isotropic temperature factors and subsequently with anisotropic displacement parameters. The function minimized was $\Sigma w(|Fo|-|Fc|)^2$. Weights, w, were eventually assigned to the data as $w=1/\sigma 2$ (fo)=$[\sigma^2(Ic)+(0.04I)^2]$. Positions for the hydrogen atoms were discovered in subsequent difference Fourier maps. The positions and isotropic temperature factors for amino hydrogen atoms and the methine hydrogens on the cyclopropyl rings were allowed to refine. Positions for all other hydrogen atoms were calculated based on geometrical considerations and held fixed in the final refinement stages along with isotropic temperature factors assigned 1.3(Beq) of the attached atom. The full matrix least-squares refinement converged (max $\Delta/\sigma=0.005$) to values of the conventional crystallographic residuals R=0.044, wR=0.054. A final difference Fourier map was featureless with maximum density of +/−0.196 e$\text{Å}^{-3}$. Values of the neutral atom scattering factors were taken from the International Tables for X-ray Crystallography.

The complete single crystal X-ray experimental data used to produce the structure.displayed in FIG. 32 for Form II is included in FIGS. 33 to 36. The parameters presented in the tables are measured in units commonly used by those skilled in the art.

TABLE 6

Intensity Measurement Data for Form II

| | |
|---|---|
| Diffractometer: | Enraf Nonius CAD4 |
| Radiation: | MoKα λ = 0.71073Å |
| Monochromator: | Graphite Single Crystal |
| Scan Technique | ω-2θ scan |
| Scan Speed: | Variable 2.50 to 6.7 deg min$^{-1}$ in ω |
| Background Measurements | Moving crystal-moving counter at each end of the scan range; scan time/background time = 2.0 |
| Range of Data: | 2° ≦ 2θ ≦ 60° |
| | 0 ≦ h ≦ 14 |
| | 0 ≦ k ≦ 8 |
| | −17 ≦ 1 ≦ 17 |
| Standard Reflections: | Three standards measured every three hours of x-ray exposure time |
| Total No. Reflections: | 2469 |
| | 2353 unique |
| Rint: | 3.4% |
| No. of Observed Data: | 1417 I≦ 3 σ(I) |
| No. of Variables: | 202 |
| p: | 0.04 |
| R: | 0.044% |
| Rw: | 0.054% |
| Goodness of Fit: | 1.403 |
| Extinction Coefficient: | 7.869(1) × 10$^{-7}$ |
| Decay Correction: | 0.9769 min, 1.1374 max |

Form IV

Flat needles were grown by slow evaporation from a 50/50 mixture of ethanol and isopropanol. Lattice parameters were determined from the setting angles of 25 reflections well distributed in reciprocal space measured on an Enraf Nonius CAD-4 diffractometer, and further described in Table 7. A full sphere of intensity data also were collected on the diffractometer using graphite monochromated copper radiation from a rotating anode source and an ω-2θ variable speed scan technique. Intensities of three monitor reflections measured at the beginning, end and every two hours of exposure time changed by at most +/−1.1%. Three orientation controls also were monitored to assess any crystal movement during the experiment. Data were corrected for Lorentz and polarization effects, and using the DIFABS algorithm, for the effects of absorption. Symmetry equivalents and Friedel related mates were averaged to obtain the final data set.

The structure was solved by direct methods using the SHELXS program series. Atomic positions were initially refined with isotropic temperature factors and subsequently with anisotropic displacement parameters. The function minimized was $\Sigma w(|Fo|-|Fc|)^2$. Weights, w, were eventually assigned to the data as w=1/σ2 (fo)=[σ²(Ic)+(0.04I)²]. Positions for the hydrogen atoms attached to nitrogens were discovered in subsequent difference Fourier maps. Positions for hydrogen atoms attached to cyclopropyl methylene carbons were calculated based on geometrical considerations and held fixed in the final refinement stages along with isotropic temperature factors assigned 1.3(Beq) of the attached atom. All other hydrogen positions were refined along with isotropic temperature factors. The full matrix least-squares refinement converged (max Δ/σ=0.01) to values of the conventional crystallographic residuals R=0.049, wR=0.071. A final difference Fourier map was featureless with maximum density of +/-0.515 eÅ$^{-3}$. Values of the neutral atom scattering factors were taken from the International Tables for X-ray Crystallography.

TABLE 7

Intensity Measurement Data for Form IV

| | |
|---|---|
| Diffractometer: | Enraf Nonius CAD4 |
| Radiation: | CuKα λ = 1,5406Å |
| Monochromator: | Graphite Single Crystal |
| Scan Technique | ω-2θ scan |
| Scan Speed: | Variable 2.50 to 6.7 deg min$^{-1}$ in ω |
| Background Measurements | Moving crystal-moving counter at each end of the scan range; scan time/background time = 2.0 |
| Range of Data: | 2° ≦ 2θ ≦ 60° |
| | -11 ≦ h ≦ 11 |
| | -15 ≦ k ≦ 15 |
| | -5 ≦ 1 ≦ 5 |
| Standard Reflections: | Three standards measured every three hours of x-ray exposure time |
| Total No. Reflections; | 3998 |
| | 2017 unique |
| Rint: | 2.5% |
| No. of Observed Data | 1662 I≦ 3 σ(I) |
| No. of Variables: | 202 |
| p: | 0.04 |
| R: | 0.049% |
| Rw: | 0.071% |
| Goodness of Fit: | 2.095 |
| Extinction Coefficient: | 1.411(1) × 10$^{-6}$ |
| Absorption Correction: | 0.911 min 1.088 max 0.997 ave |

The complete single crystal X-ray experimental data used to produce the structure displayed in FIGS. 26 and 27, for Form IV is included in FIGS. 28 to 31. The parameters presented in the tables are measured in units commonly used by those skilled in the art.

The results of a single crystal X-ray analysis are limited to, as the name implies, the one crystal placed in the X-ray beam. Crystallographic data on a large group of crystals provides powder X-ray diffraction. If the powder is a pure crystalline compound a simple powder diagram is obtained. To compare the results of a single crystal analysis and powder X-ray analysis a simple calculation can be done converting the single crystal data into a powder X-ray diagram, SHELXTL Plus (trademark) computer program, Reference Manual by Siemens Analytical X-ray Instrument, Chapter 10, p. 179–181, 1990. This conversion is possible because the single crystal experiment routinely determines the unit cell dimensions, space group, and atomic positions. These parameters provide a basis to calculate a perfect powder pattern. Comparing this calculated powder pattern and the powder pattern experimentally obtained from a large collection of crystals will confirm if the results of the two techniques are the same.

X-ray Powder Diffraction (XRD)

X-ray powder diffraction showed differences between all three forms of polymorphs. Analysis on 4×Form I samples and 4×Form II samples showed that consistent matching diffraction patterns were obtained for each set. This data is presented in FIGS. 1 and 2 herein.

Infrared Spectroscopy (IR)

The infrared absorption spectra has positively identified the existence of Forms I, II and IV. This data is presented in FIGS. 16 to 25 for compound, single crystal and crushed crystals of the various polymorphic forms.

In a compression and grinding study Form I was shown to be stable to compression and grinding, while Form II was shown to be stable to compression but not to severe grinding.

Comparison of the IR spectra of Forms I and IV shows notable differences. The prominent band in a putative methylene deformation region at 1430 cm$^{-1}$ (with a shoulder at 1442 cm$^{-1}$) for Form I is split in Form IV to give a band at 1424 cm$^{-1}$ (with a shoulder at 1434 cm$^{-1}$) and a band at 1455 cm$^{-1}$ (with a shoulder at 1466 cm$^{-1}$). The carbonyl stretching bands in Form I occur at 1648 (with a shoulder at 1656 cm$^{-1}$) and 1682 cm$^{-1}$, whereas Form IV they occur at 1656 cm$^{-1}$ and 1694 cm$^{-1}$. Weak features in the Form IV spectra at roughly 2000 and 2300 cm$^{-1}$ are absent in Form I, but these may represent overtones from the carbonyl region.

These spectra were recorded using a Spectra-Tech Plan II microscope coupled to a P-E 1760 FTIR spectrometer (64–256 scans, ratio mode, MCT detector, 4 cm$^{-1}$ resolution, dry air purge). Spectra of samples without sample preparation were obtained by mounting crystals on a diamond window. Crushed crystals were prepared using a Spectra-Tech micro-Sample Plan (a compression cell) fitted with diamond windows. A stereo microscope was used to observe the behavior of the crystals during compression. After compression, the diamond windows were separated and a spectrum was recorded of the material adhering to one of the windows.

IR spectra of single crystals of Forms I, II and IV show numerous differences as well and are readily distinguishable. There are significant differences in relative band intensities between the IR spectra of single crystals of Forms I and II and the corresponding spectra obtained from potassium bromide discs; these differences occur throughout the spectra, but are most obvious below 1700 cm-1. In particular, note the difference in relative intensities of the bands near 1530, 1440, 1260, and 800 cm-1 in the spectra of Form I, and the bands near 1540, 1420, 1260 and 1060 cm-1 in the spectra of Form II.

The spectra of crushed crystals are very similar to the corresponding KBr disc spectra. This is not surprising since both crushed crystals and KBr discs represent all molecular orientations. In many cases adequate IR transmission through crystalline samples can only be achieved by crushing.

There is poor correspondence between the single crystal and crushed crystal spectra of Form IV, with the most marked difference occurring in the regions 1660–1620, 1260–1180, 1000–920, and 800–750 cm-1. However the crushed crystal spectra of Form IV are very similar to the crushed crystal spectra of Form I. For these IR spectra, Form IV crystals were obtained in the presence of those of form II, by slow evaporation form 50:50 ethanol: isopropanol and separated by hand. Conversion of Form IV to Form I is perhaps not surprising; three dimensional X-ray diffraction data indicates that molecular conformation (aside from orientation in the cyclopropyl groups) and hydrogen-bonding (in terms of specific interactions) are similar in Forms I and IV. In forms I and IV only one of the amino hydrogens is involved in hydrogen-bonding (this contrasts with Form II, in which all hydrogen donors were found to be involved). These findings relate well to the conclusions drawn from the single crystal infrared spectra of the three forms, where the N-H stretching regions of Forms I and IV are similar, and different to Form II. Forms 1 and IV each have a band near 3455 cm-1 which is assigned to an unassociated NH function. In Form II this band is absent and it is clear that all hydrogen donors are involved in hydrogen-bonding.

IR spectra of single crystals of Form IV have been recorded on different instruments and are similar, except in the region of 1280–1260 cm$^{-1}$. This can be explained by orientation effects. A definitive spectra of Form IV is presented herein as FIG. 18.

RAMAN Spectra

Raman Spectra for Forms I, II and IV are also shown herein as FIGS. 4 to 9. As can clearly be seen, significant differences exist between the spectra of the three forms, allowing them to be readily distinguished.

Form IV, under pressure has been shown under some circumstances to convert to Form I, therefore, conventional sampling techniques, such as alkali halide discs, or Nujol mull, may not be the best way to obtain infrared spectra for this polymorph as the time involved in selecting appropriate sized crystals and obtaining a good quality spectra is high.

Raman spectroscopy provides for a quick method of distinguishing Forms I, II and IV from each other without the need for sample preparation.

Figure 4:
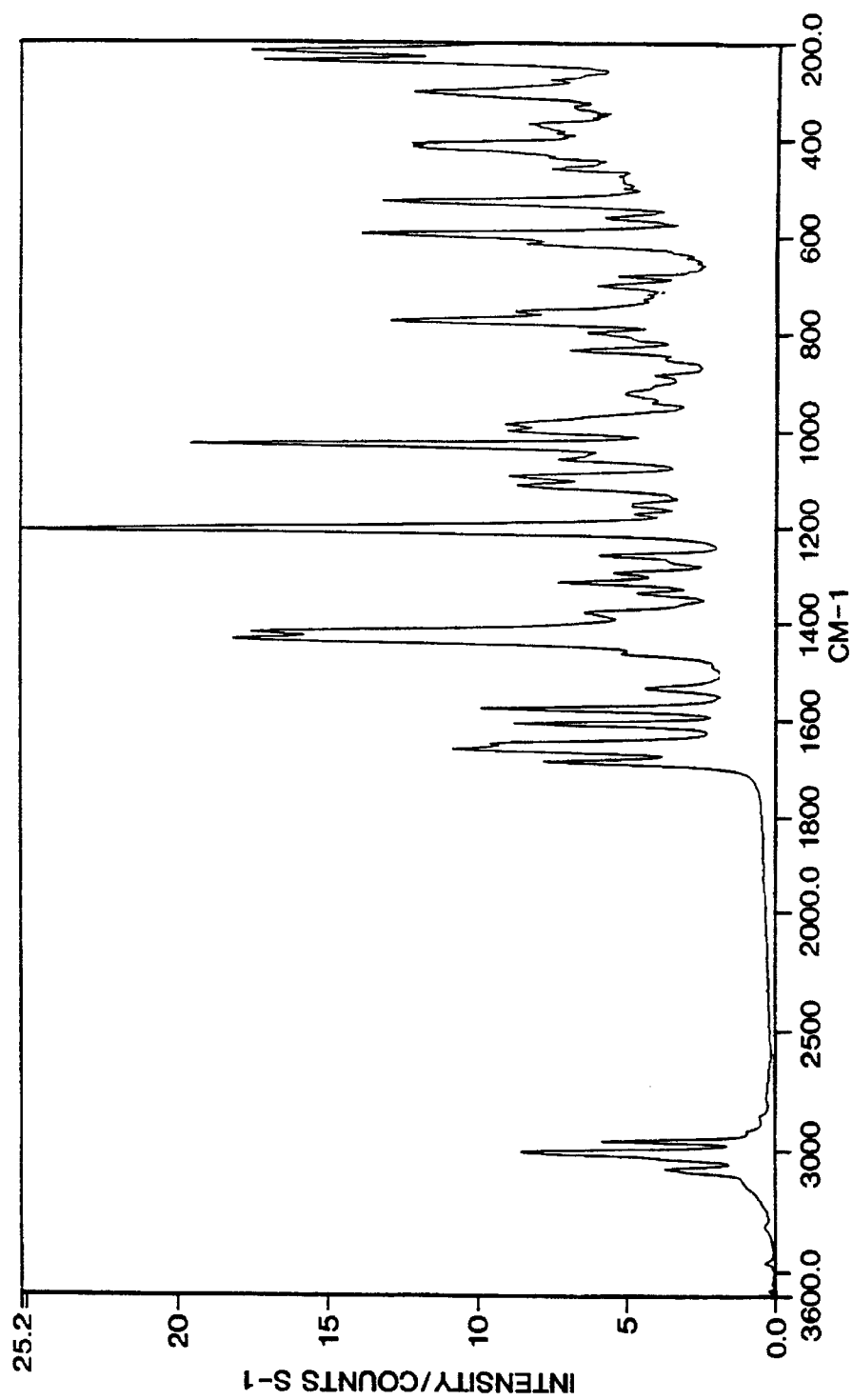
FIG. 4 is a Raman spectrum of Form I. (Vertical axis: Intensity; Lower horizontal axis: Wavenumber ($cm^{-1}$)).
Figure 5:
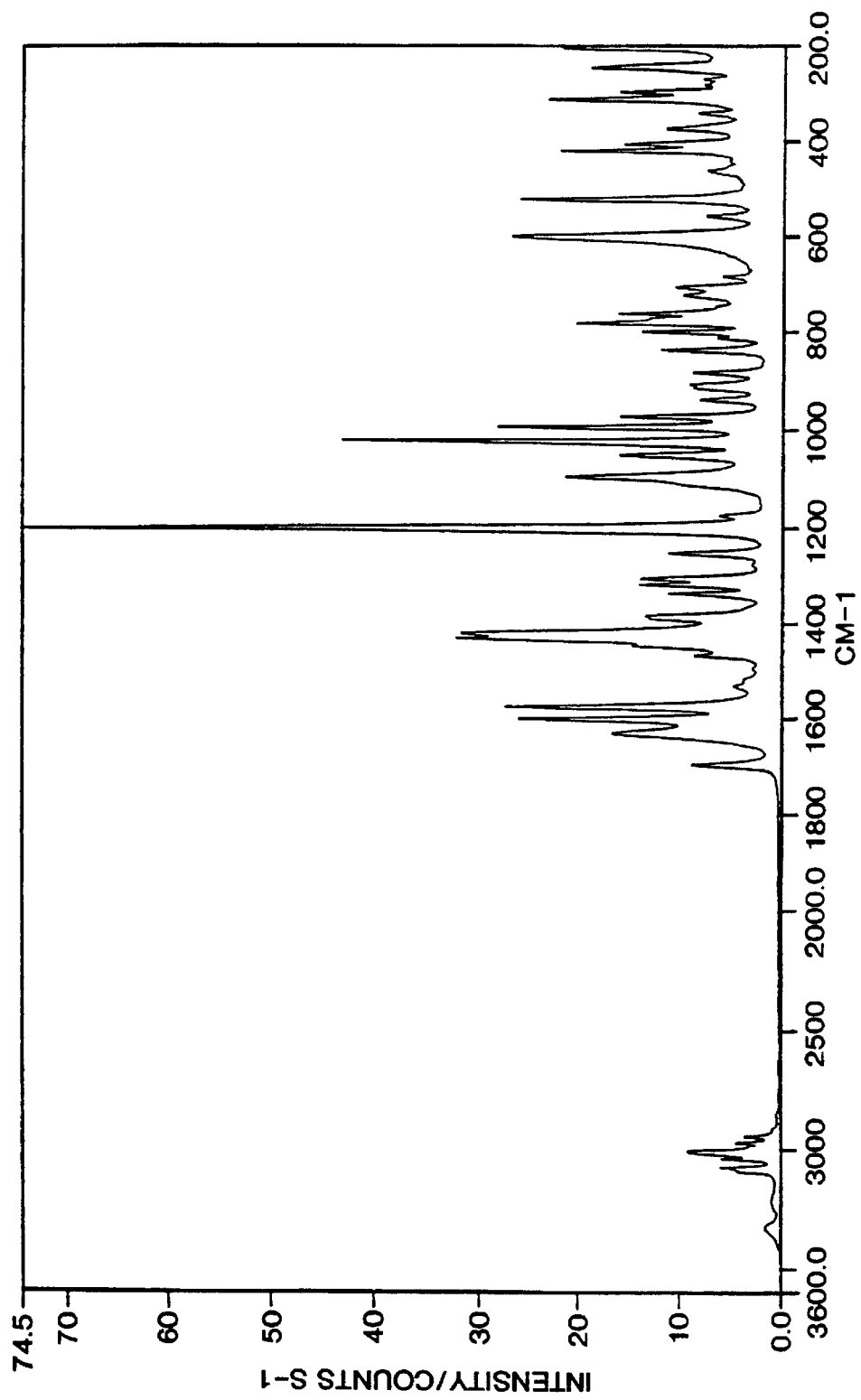
FIG. 5 is a Raman spectrum of Form II. (Vertical axis: Intensity; Lower horizontal axis: Wavenumber ($cm^{-1}$)).
Figure 6:
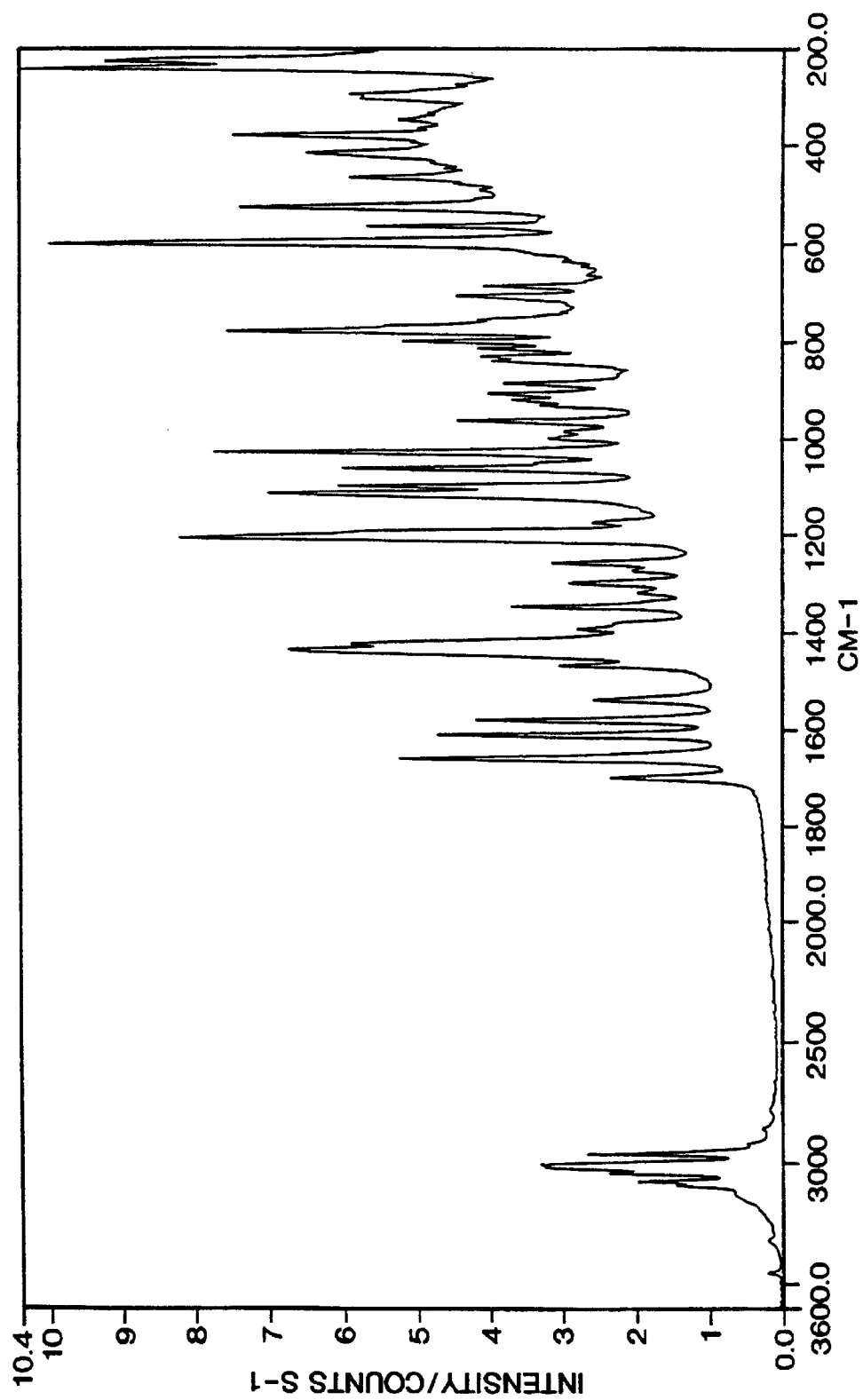
FIG. 6 is a Raman spectrum of Form IV. (Vertical axis: Intensity; Lower horizontal axis: Wavenumber (cm<-1>)).
Figure 7:
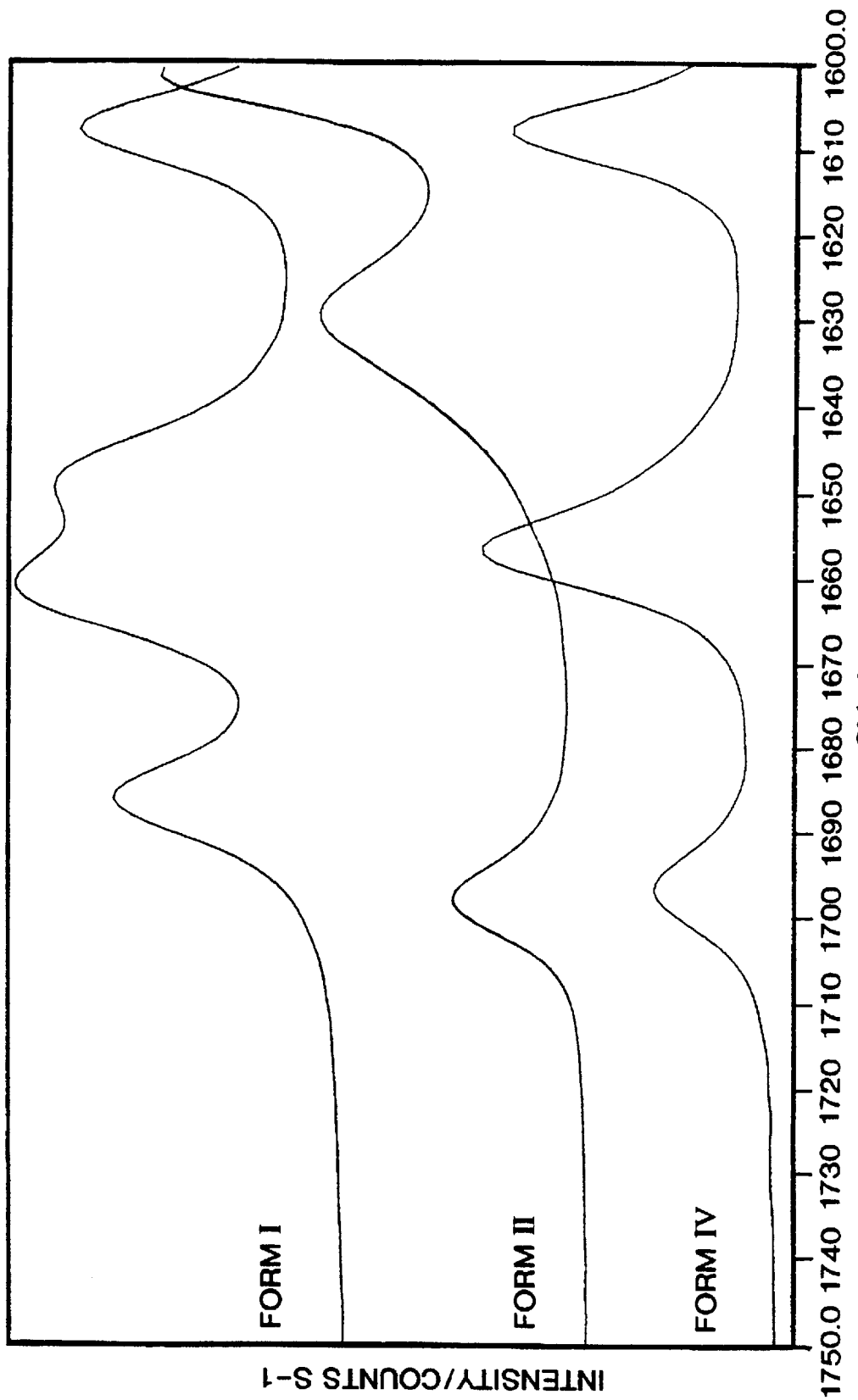
FIG. 7 is a comparison of the Raman spectra of all three for ms, Form I, II and IV-, and the carbonyl stretching region of 1750–1600 $cm^{-1}$. (Vertical axis: Intensity; Lower horizontal axis: Wavenumber (cm<-1>)).

Spectra were recorded using a Perkin-Elmer 2000 FT-Raman spectrometer equipped with an Nd:YAG NIR laser (1.064 μm). The scanning conditions were 64–256 scans, quartz beamsplitter, 4 cm-1 resolution and 1W laser power. The spectra of Form IV (FIG. 6) shows a significant amount of Raman scatter from the glass vial. This is seen as an underlying cruve with a broad maximum near 400 cm-1. Glass makes only a minor contribution to the relatively intense spectra of Forms I and II (FIGS. 4 and 5).

Figure 8:
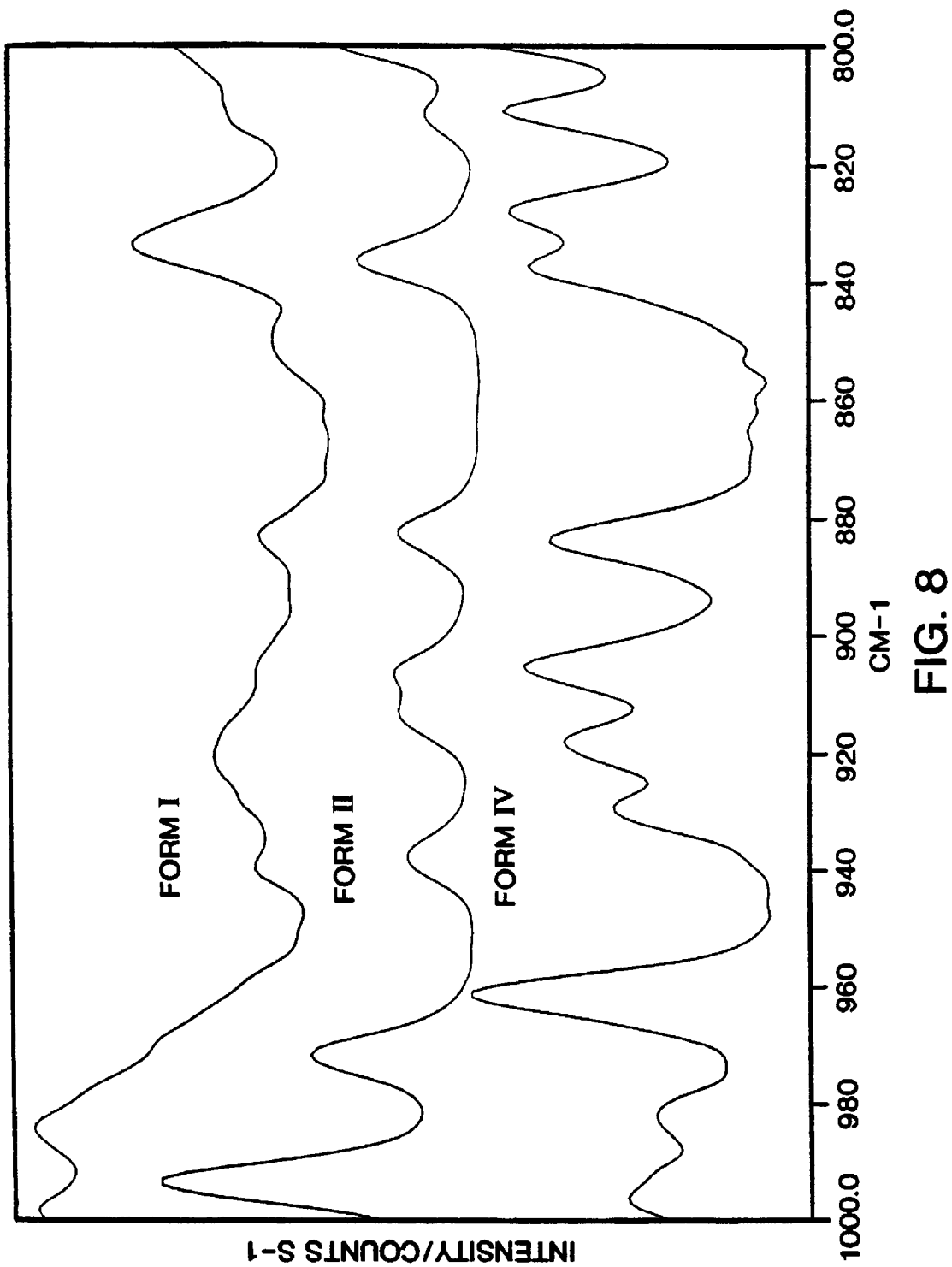
FIG. 8 is a comparison of the Raman spectra of all three forms, Form I, II and IV, and the region of 1000–800 $cm^{-1}$. (Vertical axis: Intensity; Lower horizontal axis: Wavenumber (cm<-1>)).
Figure 9:
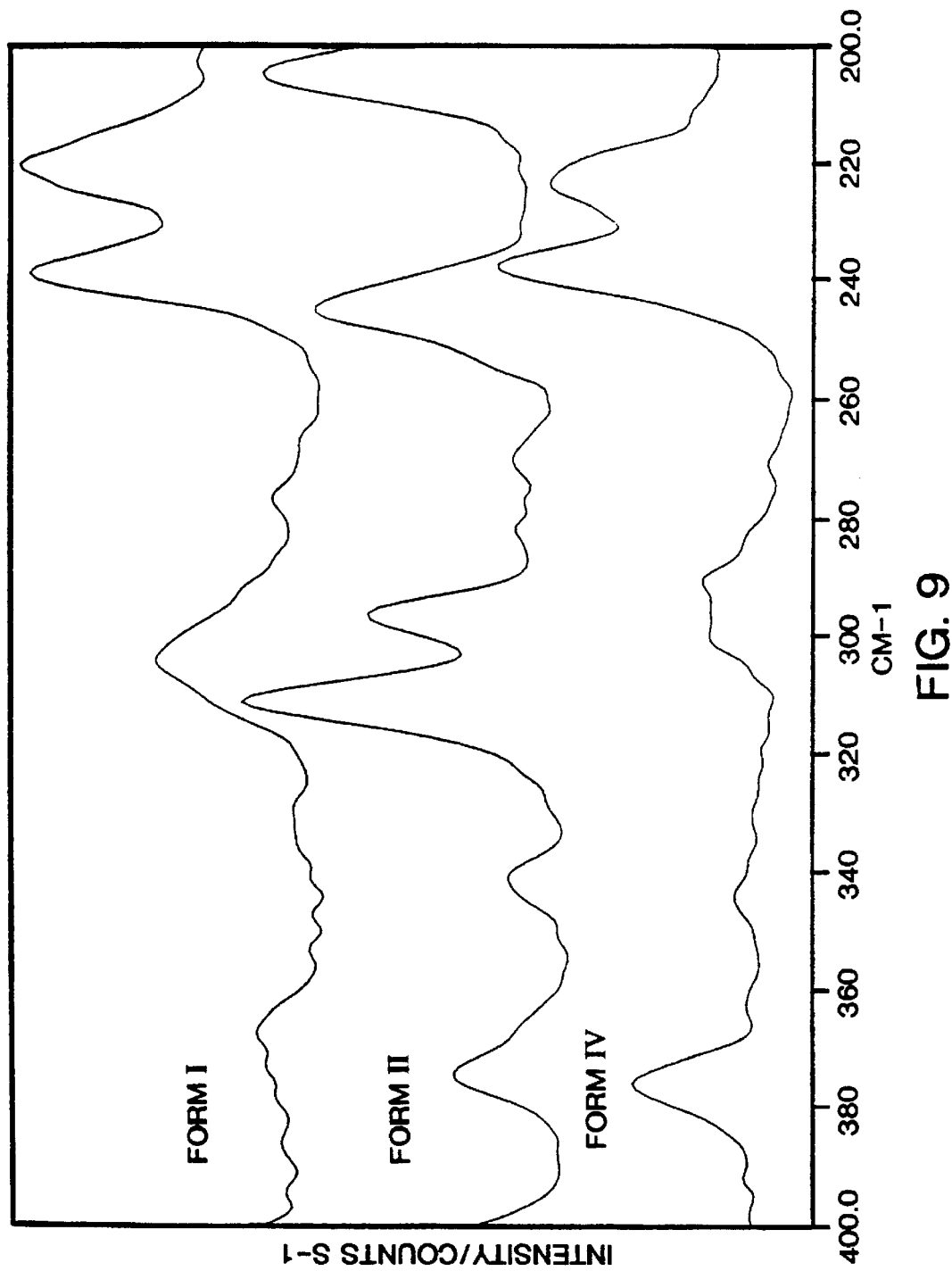
FIG. 9 is a comparison of the Raman spectra of all three forms, Form I, II and IV, and the region of 400–200 $cm^{-1}$. (Vertical axis: Intensity, Lower horizontal axis: Wavenumber (cm<-1>)).

The Raman spectra of Forms I, II and IV show numerous differences and are readily distinguishable. The carbonyl stretching region, 1750–1600 cm-1 (FIG. 7) shows the most marked difference between the forms (as was found to be the case with the IR spectra recorded from single crystals (shown herein as FIGS. 16 to 18). Significant difference exist between the three forms over the range of 1000–800 cm-1 (FIG. 8). The region 400–200 cm-1 (inaccessible when recording spectra using an infrared microscope) also shows signficant differences (FIG. 9), though sensitivity in this region is relatively poor due to detector response.

Heats of Solution

Heats of solution were determined using acetone and methanol as suitable solvents. The endothermic values are given in Table 8 below. Different polymorphic forms give rise to different heats of solution. This is demonstrated by the data obtained herein. The value of $H_T$, the heat of transition, is equal to the difference in crystal lattice energy of the two forms and is the same in both solvents. This is predicted since individual enthalpies are solvent dependent but difference are not. From these results it suggests that dissolution of Form II is more endothermic in both solvents and therefore the more stable form. Heats of solution for Form IV are in progress.

TABLE 8

| Form | Methanol (kcal/mol) | Acetone (kcal/mol) |
|---|---|---|
| 1 | 4.81 | 3.93 |
| 2 | 6.47 | 5.59 |
| Δ H$_Y$ | 1.66 | 1.66 |

Thermal Analysis

Differential Scanning Calorimetry (DSC) could not differentiate the three forms of Cipamfylline. In each case thermograms showed melting only with similar onset and peak temperatures, typically T$_e$ 312, T$_p$ 314° C. However, when the heating rate was reduced sufficiently, the melting endotherm appeared as a fused melt, i.e. two components melting. This behavior was common to both Forms I and II.

Thermomicroscopic observations showed that all three forms sublime. The onset of sublimation was different for each form and continued over a wide temperature range (130–290° C. on a non-calibrated instrument). This is not evident on the DSC thermograms. Melting occurred over a range (310–323° C. on a non-calibrated instrument) for all three forms. The possibility of two components melting consecutively could not be distinguished. The sublimate was collected for all three forms and analyzed by IR and NMR. This showed that Form I had been produced.

Forms I, and II were annealed and were found to have converted to Form I by IR. The annealing procedure consisted of heating at 10° C./min from ambient to ca. 250° C. and holding at this point for ½–1 hour, then allowing the sample to cool slowly to room temperature.

The above thermal experiments appear to indicate that Form I is the most stable form. This could explain the similarity in melting points of the three forms.

Synthetic Methods of Recrystallization

Various batches of Cipamfylline were prepared by the same route and the final recrystallization solvent and rate of cooling were varied as shown in Table 9 below.

TABLE 9

| Solvent | Rate of Cooling | Recovery | Polymorph produced |
|---|---|---|---|
| Ethanol | slow | 75% | Form II |
| Ethanol | very slow | 75% | Form II |
| Methanol | slow | 70% | Form II |
| Acetone | fast | 22% | Form I |
| Tetrahydrofuran | fast | 33% | Forms I and III* |
| Tetrahydrofuran | slow | 58% | Form I |

*In the case of THF (fast), it appears that the Form I produced is contaminated with another form, Form III. All data indicates that Form III could be a polymorph, but has not been characterised as it always seems to be produced in mixtures. Slow cooling in this solvent produced Form I.

Form II Recrystallization

Another experimental procedure used to recrystallize Form II from a solvent mixture of methanol/2-butanone as follows: Solid material from a cipamfylline sample was added to an aliquot of 2-butanone in a glass vial and warmed gently on a hot plate with sting. Methanol was added dropwise to the stirring warm solution until all solid material appeared to have dissolved. Small holes were placed in the plastic vial cap and the clear, colorless solution was left to evaporate slowly in a hood at ambient temperature. Rectangular crystals of Form II appeared within 11 days.

In yet another study, Cipamfylline (1 g) was dissolved in EtOH (55 volumes) and cooled the solutions to 20–25° C. over 1 hour and 4 hours respectively. The results are shown in Table 10 below.

Table 10

Recrystallisation of Cipamfylline from EtOH

| Example | scale (mmol) | time to cool[a] to 20–25° (h) | recovered yield (%) | polymorphic[b] form |
|---|---|---|---|---|
| 1 | 3.6 | 1 | 74.9 | II |
| 2 | 3.6 | 4 | 75.2 | II | notes:
[a]Time to cool from reflux (~78° C.) to about 20–25° C.
[b]Determined by IR Spectroscopy In both cases, cooling over a prolonged period (≧1 h) gave Cipamfylline in polymorphic form II.

Form IV Recrystallization

In another experimental procedure for recrystallization of Form IV, solid material from sample a Cipamfylline sample was added to an aliquot of isopropanol in a glass vial and warmed gently on a hot plate with stirring. An equal volume of ethanol was added and stirring continued until all solid material appeared to have dissolved. Small holes were placed in the plastic vial cap and the clear solution was left to evaporate slowly in a hood at ambient temperature. Over a short time rectangular crystals of Form II appeared followed in several days by needles, one of which was used for the structure determination of Form IV.

Form I Recrystallization

In another experimental procedure for purification of Cipamfylline, (15.5 g) was dissolved in n-propanol (300 mL) at reflux. Cooling to room temperture lead to precipitation of a purified product, of Form I which was isolated by filtration and dried at 70° C. overnight. Wt. recovered Cipamfylline=11.96 g; Yield=63%. Alternative solvents, such as n-propanol/water, 3:1 also lead to similar yields and results.

As noted above, 1-Propanol is a preferred solvent to prepare Cipamfylline in polymorphic form I. The recrystalization procedure with 1-propanol has been carried out on larger scale, approx. 2 kg scale with repeated success.

Cooling times from 97° C. to ambient temperature have varied from about 70 minutes to overnight (approx. 8 to 12 hours). Form I has been formed reproducibly.

This process can be summarised below:

Crude BRL-61063 (2.06 kg) was dissolved in 1-propanol (40 L) at about 97° C. The reaction was then cooled to about 18° C. over about 70 minutes. The resulting suspension was filtered, the solid washed with prechilled 1-propanol (3×0.6 L) and dried in air at about 50° C. overnight to give purified Cipamfylline (1.85 kg, 90%) Form I product.

In yet another recrystallisation study, similar to that shown above in Table 9, again using MeOH, THF and acetone, the results are reported in Table 11 below.

TABLE 11

Recrystallisation of Cipamfylline form various solvents[a]

| entry | solvent | conc[n] (g/ml) | time to cool[b] to 20–25° C. (min) | recovered yield (%) | polymorphic[c] form |
|---|---|---|---|---|---|
| 1 | MeOH | 0.018 | 60 | 70 | II |
| 2 | Acetone | 0.004 | 40 | 64 | II[d] + I |
| 3 | Acetone | 0.004 | ~1[e] | 22 | I |
| 4 | Acetone | 0.004 | ~1[e] | 49 | I |
| 5 | THF | 0.017 | ~1[e] | 33 | I + III |
| 6 | THF | 0.017 | 60 | 58 | I | notes:
[a]General method: x g of BRL-61063 were suspended in y ml of the appropriate solvent and heated to reflux whereupon dissolution occurred. The solution was then cooled over the appropriate time and the product isolated by filtration.
[b]Time to cool from reflux to 20–25° C.
[c]Determined by IR Spectroscopy
[d]Predominantly form II, some form I.
[e]Crash cooling of solution with an ice bath.

These data (Table 11) show that slow crystallisation of BRL-61063 from MeOH (entry 1) provided product in polymorph form II. Polymorph from II was the predominant form obtained from slow cooling of an acetone solution of BRL-61063 (entry 2). Crash cooling of an identical solution (entry 3) gave BRL-61063 in exclusively form I. The fast cooling experiment was repeated and gave form I product (entry 4) confirming the original observation.

BRL-61063 was dissolved in THF and fast cooling led to isolation of material existing in polymorphic forms I and III (entry 5). Form I was exclusively obtained from slow cooling (entry 6).

These experiments therefore provide for another aspect of the present invention which is a process for producing Form I, which process comprises placing crude Cipamfylline in an organic solvent, dissolving the crude product by heating to about reflux temperature and then cooling to crystalize out the desired form.

For Form I, the preferred solvent is 1-propanol, acetone of THF, more preferably 1-propanol. For Form I the reaction cooling time is determined by the minimum time to cool from reflux, or from the temperature at which dissolution of the crude product occurred in a solvent, i.e. from a minimum time to crash cooling a solution, which on a commerial scale is about 15 minutes. Preferably, the minimum cooling time is a realistic time period of about 50–70 minutes to what ever is desired, such as overnight (i.e. 8 to 12 hours). Preferably, the cooling time is about 60–70 minutes with a range to about 120 minutes to overnight if desired. The cooling temperature is preferably from about 0° C. to about 25° C., preferably from about 15° C. to about 25° C., more preferably from about 18° C. to about 25° C. Also, ethanol is an alternative solvent, but only if crash cooling is used. If Form II is desired than ethanol, or methanol, is useful if a long cooling time is used 9 (see table 9 or 11).

If THF is used as a solvent to produce Form I, than slow cooling is necessary, and if acetone is used, than fast cooling is necessary as well.

It is recognized that other combinations of solvents under suitable conditions may be used herein, these combinations could include admixture with water, or with other organic solvents, such as DMF, heptanes, MeCN, n-butanol, isopropanol, ethyl acetate, TBME, toluene, decalin, etc. All of these are included within the meaning of a modifications or improvements of the specifically exemplified embodiments herein. It is recognized that this is within the skilled artisans means to produce the optimal solvent for use for recrystallization on a laboratory and commercial scale using the disclosures herein.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for producing a crystalline polymorph of 1,3-di-cyclopropylmethyl-8-amino xanthine, Form I, which process comprises
   a) dissolving 1,3-di-cyclopropylmethyl-8-amino xanthine in 1-propanol or in a 1-propanol:water admixture; and
   b) cooling the solution to crystallize out of solution the desired polymorphic Form I, as characterized in any one of FIGS. 1, 4, 20, or wherein Form I exhibits a single crystal X-ray crystallographic analysis with (a) crystal parameters that are approximately equal to the following:

| | |
|---|---|
| Crystal shape (mm) | Flat needles |
| Crystal dimensions | 1.0 × 0.12 × 0.08 mm |
| Crystal color | Colorless |
| Space Group | P1 triclinic #2 |
| Temperature | 295 K |
| Cell Constants | a = 10.829(2)Å |
| | b = 12.636(2)Å |
| | c = 5.105(3)Å |
| | alpha ($\alpha$) = 99.48(4) |
| | beta ($\beta$) = 91.53(4) |
| | gamma ($\gamma$) = 83.84(3) |
| Volume | 685.0(8)Å$^3$ |
| Molecules/unit cell (Z) | 4 |
| Density, ($\rho$) g/cm$^{-3}$ | 1.354 |
| $\mu$ | 7.362 cm$^{-1}$ |
| F(000) | 292 | the atomic positions of all atoms relative to the origin of the unit cell as represented in the tables of FIGS. 12 to 15.

2. The process according to claim 1 wherein the temperature for crystallization of the Form I polymorph from the 1-propanol or 1-propanol:water admixture of part (a) is from about 0 to about 25° C.

3. The process according to claim 2 wherein the time for crystallization of the polymorph from the 1-propanol or 1-propanol:water admixture of part (a) is from about 15 to about 120 minutes.

4. The process according to claim 1 wherein the xanthine is dissolved by heating the 1-propanol to reflux conditions.

* * * * *